United States Patent
Kim et al.

(10) Patent No.: US 9,844,575 B2
(45) Date of Patent: Dec. 19, 2017

(54) PHARMACEUTICAL COMPOSITION AND FUNCTIONAL FOOD COMPRISING NATURAL EXTRACTS FOR PREVENTING OR TREATING DIABETIC COMPLICATIONS OR ANGIODEMA

(71) Applicant: KOREA INSTITUTE OF ORIENTAL MEDICINE, Daejeon (KR)

(72) Inventors: Jin Sook Kim, Seoul (KR); Jung Hyun Kim, Seoul (KR); Chan Sik Kim, Daejeon (KR); Young Sook Kim, Daejeon (KR); Eun Jin Shon, Daejeon (KR); Yun Mi Lee, Daejeon (KR); Dong Ho Jung, Daejeon (KR); Ik Soo Lee, Daejeon (KR); Gyu Hyeong Jo, Daegeon (KR); Joo Hwan Kim, Gyeonggi-do (KR)

(73) Assignee: KOREA INSTITUTE OF ORIENTAL MEDICINE, Daejeon (KR)

(*) Notice: Subject to any disclaimer, the term of this patent is extended or adjusted under 35 U.S.C. 154(b) by 46 days.

(21) Appl. No.: 14/759,471

(22) PCT Filed: Jan. 10, 2014

(86) PCT No.: PCT/KR2014/000292
§ 371 (c)(1),
(2) Date: Jul. 7, 2015

(87) PCT Pub. No.: WO2014/109587
PCT Pub. Date: Jul. 17, 2014

(65) Prior Publication Data
US 2015/0343005 A1    Dec. 3, 2015

(30) Foreign Application Priority Data

Jan. 10, 2013 (KR) .................. 10-2013-0003125
May 3, 2013 (KR) .................. 10-2013-0050320

(51) Int. Cl.
| | |
|---|---|
| *A61K 36/00* | (2006.01) |
| *A61K 36/25* | (2006.01) |
| *A61K 31/155* | (2006.01) |
| *A61K 36/708* | (2006.01) |
| *A61K 36/488* | (2006.01) |
| *A61K 36/16* | (2006.01) |
| *A61K 36/482* | (2006.01) |
| *A61K 36/45* | (2006.01) |
| *A61K 36/73* | (2006.01) |
| *A61K 36/87* | (2006.01) |
| *A61K 36/718* | (2006.01) |
| *A23L 33/105* | (2016.01) |

(52) U.S. Cl.
CPC ............ *A61K 36/25* (2013.01); *A23L 33/105* (2016.08); *A61K 31/155* (2013.01); *A61K 36/16* (2013.01); *A61K 36/45* (2013.01); *A61K 36/482* (2013.01); *A61K 36/488* (2013.01); *A61K 36/708* (2013.01); *A61K 36/718* (2013.01); *A61K 36/73* (2013.01); *A61K 36/87* (2013.01); *A23V 2002/00* (2013.01)

(58) Field of Classification Search
None
See application file for complete search history.

(56) References Cited

FOREIGN PATENT DOCUMENTS

| KR | 10-1998-033798 | 8/1998 |
|---|---|---|
| KR | 10-2009-0129936 | 12/2009 |
| KR | 10-2010-0108869 | 10/2010 |
| WO | WO/2008/065457 | 6/2008 |

OTHER PUBLICATIONS

Zou et al, Research advance in anti-diabetic mechanism of alkaloids in Coptis chinensis. Zhongcaoyao (2004), 35(11), App.2-App.5.*
Ibrar et al, Hypoglycemic activity of Hedera helix L. leaves and the possible mechanism of action. Scientific Khyber, (Jan. 2000) vol. 13, No. 1, pp. 1-7.*
Extended European Search Report for Application No. 14737578.6 dated Aug. 17, 2016.
Yuan, L. et al. "Hypoglycemic and Hypocholesterolemic Effects of *Coptis chinensis* Franch Inflorescence." *Plant Foods for Human Nutrition*, 61(3): 139-144. 2006.
Zhen, Z. et al. "Anti-Diabetic effects of a *Coptis chinensis* Containing New Traditional Chinese Medicine Formula in Type 2 Diabetic Rats." *The American Journal of Chinese Medicine*. 39(1): 53-63. 2011.
Ibrar, Muhammad et al. "Hypoglycemic Activity of *Hedera Helix* L. Leaves and the Possible Mechanism of Action." *Pak. J. Bot.*, 35(5): 805-809, 2003.
International Search Report for PCT/KR2014/000292 dated May 2, 2014 (Korean with English translation).

* cited by examiner

*Primary Examiner* — Qiuwen Mi
(74) *Attorney, Agent, or Firm* — Norton Rose Fulbright US LLP

(57) ABSTRACT

The present invention relates to a pharmaceutical composition and a health functional food composition for prevention, treatment or amelioration of diabetic complications or angioedema containing a mixed extract of *Hedera helix* leaves and *Coptis chinensis* as an active ingredient. More specifically, the present invention relates to a pharmaceutical composition and a health functional food composition for prevention, treatment or amelioration of diabetic complications or angioedema further containing an extract of *Rheum palmatum, Puerariae radix, Ginkgo* leaves, *Cassiae semen*, blueberry, bilberry, raspberry, or grape seeds as an active ingredient, in addition to the mixed extract of *Hedera helix* leaves and *Coptis chinensis*.

13 Claims, 17 Drawing Sheets

FIG. 12

PHARMACEUTICAL COMPOSITION AND FUNCTIONAL FOOD COMPRISING NATURAL EXTRACTS FOR PREVENTING OR TREATING DIABETIC COMPLICATIONS OR ANGIODEMA

CROSS-REFERENCE TO RELATED APPLICATIONS

This application is a national phase application under 35 U.S.C. §371 of International Patent Application No. PCT/KR2014/000292 filed Jan. 10, 2014, which claims priority to and the benefit of Korean Patent Applications No. 10-2013-0003125, filed Jan. 10, 2013, and No. 10-2013-0050320, filed May 3, 2013. The entire contents of the referenced applications are incorporated herein by reference.

TECHNICAL FIELD

The present invention relates, in general, to a pharmaceutical composition and a health functional food composition for prevention, treatment or amelioration of diabetic complications or angioedema containing a mixed extract of *Hedera helix* leaves and *Coptis chinensis* and, more particularly, to a pharmaceutical composition and a health functional food composition for prevention, treatment or amelioration of diabetic complications or angioedema further containing an extract(s) of *Rheum palmatum, Puerariae radix, Ginkgo* leaves, *Cassiae semen*, blueberry, bilberry, raspberry, or grape seeds as an active ingredient, in addition to the mixed extract of *Hedera helix* leaves and *Coptis chinensis*.

BACKGROUND ART

Generally, diabetes mellitus is a globally occurring adult disease. Recently, the occurrence rate of diabetes mellitus in Korea has reached 10%, and the global diabetes mellitus population has already passed 240 million. According to a report by the Journal of the American Medical Association (JAMA) in 2009, the number of diabetics globally is expected to grow to 380 million, and among them, about 60% of the diabetes mellitus cases will occur in Asian regions. In particular, the onset of diabetes mellitus has advanced to young adults, and the occurrence of complications has become unavoidable due to extended life expectancy.

Diabetic retinopathy occurs in diabetics within 10 years from the onset of diabetes mellitus with a probability of 60% or higher, and within 20 years with a probability of 90% or higher. Particularly in Korea, the medical expenses for the treatment of peripheral circulatory disorders, which are diabetic complications, has increased from 80.7 billion Korean won in 2006 to 153 billion Korean won, and the expenses for diabetic retinopathy have increased from 32.7 billion Korean won to 50.5 billion Korean won, showing a 54.4% increase. Diabetic retinopathy is a type of microangiopathy caused by chronic diabetes mellitus, and is characterized by having an altered permeability and vaso-occlusion of retinal blood vessel, change in ischemia, neovascularization, and subsequent fibrovascular proliferation. Diabetic retinopathy is the most frequent cause of postnatal blindness in adults, and about 12,000 to 24,000 people in the USA become blind due to diabetes mellitus every year. In fact, a laser treatment or a surgery of vitreous body is not sufficient to end the progression of blindness and about 8% of the treated diabetics ultimately become blind. Accordingly, early discovery of diabetic retinopathy, prevention of the progression of diabetic retinopathy, and early treatment are essential, but the exact etiology of diabetic retinopathy still remains unknown and thus its effective treatment is limited.

More than 80% of diabetic neurosis occurs in diabetic patients due to accumulation of metabolic side products, myelin loss in neurons, and changes in microvessels. Generally, the treatment of neurosis cannot be easily performed, and thus its prevention by regulation of blood glucose level or alleviation of symptoms such as pain is often performed instead.

Peripheral vascular disease can be discovered in 45% of patients after a duration of about 20 years of diabetes mellitus since its onset, which normally accompanies arterial stiffness and circulatory disturbance, and its complete cure is difficult. For example, foot ulcer is a dreadful complication which requires surgical removal of the four limbs.

Diabetic nephropathy patients require hemodialysis due to improper renal functions caused by chronic diabetes mellitus, and may ultimately require kidney transplantation.

Chronic diabetes mellitus causes functional disorders in blood vessels and lymphatic ducts, thereby releasing tissue fluids and blood or making them stagnant. When these symptoms appear in the retinal blood vessels, there occur macular edema and macular degeneration due to an abnormal change in drusen, etc., whereas when this symptom occurs in veins there occur varices; when these symptoms occur in lymphatic ducts there occurs lymphedema; and when these symptoms occur histologically in lower limbs there occur varicose veins. Accordingly, these are accompanied by visual impairment, blindness, lower limb numbness, pain, paresthesia, and nocturnal pain. However, there is no therapeutic agent available and thus only pharmaceutical drugs similar to antioxidants are being administered (Diabetes, the $4^{th}$ edition, Korean Diabetes Association, Korea Medical Book Publisher, 2011, p. 577).

For the treatment of macular degeneration, high-priced intravitreal antivascular endothelial growth factor therapy or laser therapy may be used, but these therapies still cannot cure the disease and thus the patients must tolerate fatal visual impairment.

Meanwhile, the formation of advanced glycation endproducts (AGEs) is one of the representative factors in inducing diabetic complications. Nonenzymatic glycation of proteins is a reaction for producing advanced glycation endproducts (AGEs) by a condensation reaction (Maillard reaction) between an amino group such as a lysine residue of a protein and a reducing sugar, without an enzymatic reaction. Unlike the reversible Amadori type early glycation products, the advanced glycation endproducts are irreversible reaction products. Therefore, once the advanced glycation endproducts are produced, they are not decomposed but accumulated in tissues during the lifetime of the proteins, although the blood glucose level returns to normal, thereby abnormally changing the structures and functions of the tissues and inducing complications such as diabetic retinopathy, diabetic cataract, diabetic nephropathy, diabetic neuropathy, diabetic cancer, diabetic heart disease, diabetic osteoporosis, foot ulcer or diabetic arteriosclerosis, etc. (Vinson, J. A. et al., 1996, J. Nutritional Biochemistry 7: 559-663; Smith, P. R. et al., 1992, Eur. J. Biochem., 210: 729-739).

DISCLOSURE

Technical Problem

The present inventors have confirmed that a composition containing a mixed extract of *Hedera helix* leaves and *Coptis chinensis* as an active ingredient, or a mixed composition prepared by adding an extract(s) of *Rheum palmatum, Puerariae radix, Ginkgo* leaves, *Cassiae semen*, blueberry, bilberry, raspberry, or grape seeds to the composition containing the mixed extract of *Hedera helix* leaves and *Coptis chinensis* exhibited excellent effects for the prevention or treatment of diabetic complications such as inhibition of formation of advanced glycation endproducts, inhibition of formation of vascular endothelial growth factor, inhibition of blood-retinal barrier breakage and optic nerve breakage, improvement of motor neuron conduction velocity, foot ulcer, etc., and angioedema, thereby completing the present invention.

Technical Solution

In order to accomplish the above object, the present invention provides a pharmaceutical composition and a health functional food composition containing a mixed extract of *Hedera helix* leaves and *Coptis chinensis* capable of preventing, treating or ameliorating diabetic complications or angioedema, as an active ingredient.

Advantageous Effects

According to the present invention, the mixed extract of *Hedera helix* leaves and *Coptis chinensis* of the present invention has excellent effects of inhibiting blood-retinal barrier breakage, formation of vascular endothelial growth factor, and formation of advanced glycation endproducts, which are indicators of diabetic complications, and thus can be usefully used as a component for a pharmaceutical drug or a health functional food derived from a natural product without any adverse effects to humans, while being effective for the prevention and treatment of diabetic complications or angioedema.

DESCRIPTION OF DRAWINGS

FIG. 12 shows results of the inhibitory effect of COPH or (COPH+MET) against the formation of reactive oxygen species (ROS) and reactive nitrogen species (RNS), in the retinal tissues of a diabetic animal model.

BEST MODE

Figure 1:
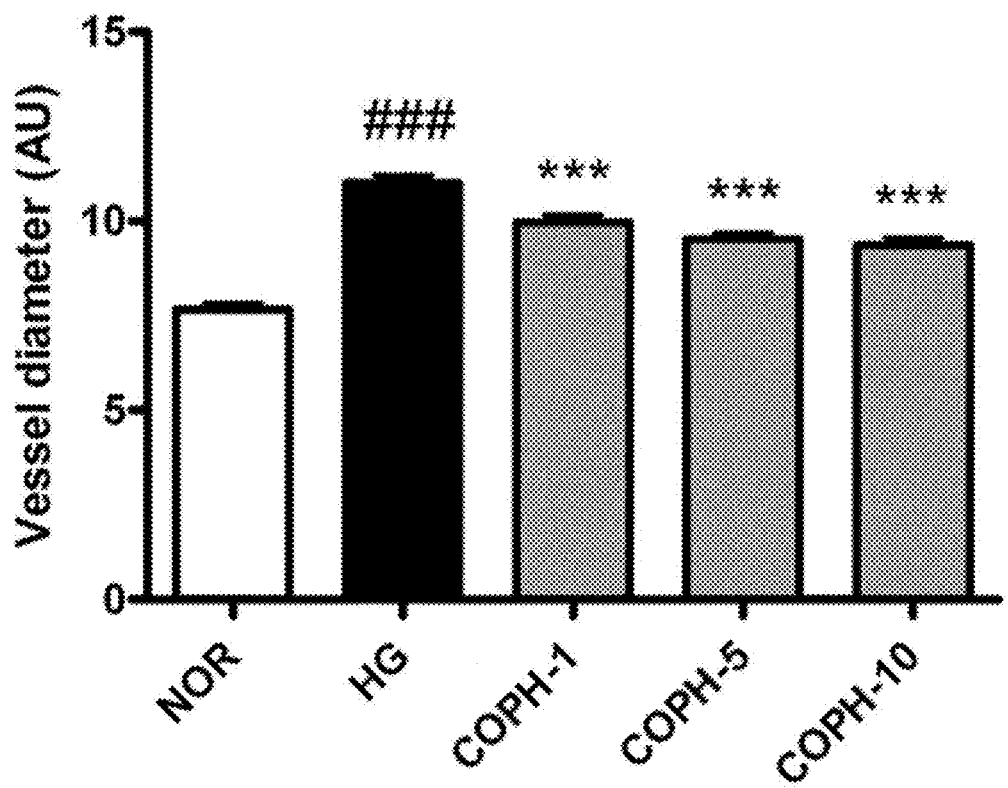
FIG. 1 shows a result of the inhibition of diameter increase of a vitreous body retinal vessel in a zebrafish model by a mixture of a *Hedera helix* leaf extract and *Coptis chinensi* extract (COPH).

The present invention provides a pharmaceutical composition for prevention or treatment of diabetic complications or angioedema containing a mixed extract of *Hedera helix* leaves and *Coptis chinensis* as an active ingredient.

Additionally, the composition may further contain an extract(s) of *Rheum palmatum, Puerariae radix, Ginkgo* leaves, *Cassiae semen*, blueberry, bilberry, raspberry or grape seeds, in addition to the mixed extract of *Hedera helix* leaves and *Coptis chinensis*.

As used herein, the term "a mixed extract of *Hedera helix* leaves and *Coptis chinensis*" refers to a mixture between a *Hedera helix* leaf extract and a *Coptis chinensis* extract; or an extract prepared by extracting the mixture of *Hedera helix* leaves and *Coptis chinensis*.

"*Hedera helix* leaf" is known to have effects of alleviating neuralgia and rheumatism. Preferably, a *Hedera helix* leaf extract is prepared by extracting using water, methanol, ethanol, butanol, or a mixed solvent thereof, but is not limited thereto.

"*Coptis chinensis*" is used for the treatment of gastritis, stomachache, vomiting, etc. Preferably, a *Coptis chinensis* extract is prepared by extracting using water, methanol, ethanol, butanol, or a mixed solvent thereof, but is not limited thereto.

"*Rheum palmatum*" is known to have a stomach-strengthening effect, and also serves as a mitigator for habitual constipation.

"*Puerariae radix*" is also known as *Pueraria thynbergiana* (*P. lobata, P. thomsonii*), and is used for the treatment of dyspepsia, stomach ache, colds, and melena.

"*Ginkgo* leaf" is known to have an antioxidation effect.

"*Cassiae semen*" is a seed of *Cassia tora* and *C. obtusifolia*, and is known to have effects of lowering blood pressure and cholesterol level.

"*Vaccinium* spp. (blueberry)" is known to have effects of antioxidation, antiulcer, antiinflammation, intestinal regulation, etc.

"Bilberry" is known to have effects of eyesight protection and lowering cholesterol level.

"Raspberry" is known to have effects of antiinflammation, antioxidation, anti-*Helicobacter pyroli* activity, etc.

"Grape seeds" is known to have effects of fatigue recovery, antivirus, etc.

Preferably, the extracts of *Rheum palmatum, Puerariae radix, Ginkgo* leaves, *Cassiae semen*, blueberry, bilberry, raspberry, or grape seeds may be prepared by extracting *Rheum palmatum, Puerariae radix, Ginkgo* leaves, *Cassiae semen*, blueberry, bilberry, raspberry, or grape seeds using water, methanol, ethanol, butanol, or a mixed solvent thereof, but are not limited thereto.

The mixed extract between the *Hedera helix* leaf extract and the *Coptis chinensis* extract may be prepared by mixing them at a ratio of 10:1 to 1:10, or prepared by mixing the *Hedera helix* leaves and a *Coptis chinensis* at a ratio of 10:1 to 1:10, followed by extraction, but is not limited thereto.

Preferably, the composition may further contain metformin in addition to the *Hedera helix* leaf extract and the *Coptis chinensis* extract. If metformin is added, the effect of the composition may significantly increase. Preferably, metformin may be added in the amount of 1- to 7-fold relative to the total weight of the mixed extract of *Hedera helix* leaves and *Coptis chinensis*.

Preferably, the above extraction may be performed via room temperature extraction, hot water extraction, cold immersion extraction, reflux cooling extraction, ultrasonification extraction, supercritical extraction, or vapor extraction, but is not limited thereto.

Additionally, the *Hedera helix* leaf extract may contain a fraction of *Hedera helix* leaf extract.

As used herein, the term "fraction" refers to a particular component obtained by suspending the *Hedera helix* leaf extract in water followed by sequential fractionation using solvents with different polarities. The solvents may be ethyl acetate, n-butanol, or water.

Specifically, the fraction of the *Hedera helix* leaf extract may be obtained by suspending the ethanol extract of the *Hedera helix* leaves in water, followed by fractionation with ethyl acetate; or may be a butanol fraction or a water fraction obtained by fractionation of the water fraction, which was obtained by suspending the ethanol extract of the *Hedera helix* leaves in water followed by fractionation with butanol.

Additionally, the fraction of the *Hedera helix* leaf extract may be a butanol fraction or a water fraction obtained by suspending the ethanol extract of the *Hedera helix* leaves in water, followed by fractionation with butanol.

As used herein, the term "diabetic complications" refers to a symptom induced when diabetes mellitus is sustained for a long period of time. Diabetic complications differ from the onset criteria and determination criteria of diabetes mellitus. Therefore, the therapeutic agents for diabetic complications are used separately from those for diabetes mellitus. Examples of representative diabetic complications may include diabetic eye disease, diabetic retinopathy, diabetic cataract, diabetic nephropathy, diabetic neuropathy, diabetic cancer, diabetic heart disease, diabetic osteoporosis, diabetic arteriosclerosis, coronary artery disease, peripheral artery disease, and peripheral vascular disease such as cerebrovascular disease due to diabetes mellitus.

As used herein, the term "angioedema" refers to a symptom, in which the permeability of the blood vessels located deep inside the skin or underneath the skin, or beneath the mucous membrane is increased, thereby causing the body fluids therein to leak out and gather around the neighboring tissues. Examples of angioedema may include varicose veins, macular edema, macular degeneration, etc.

In the present invention, it was confirmed that a composition containing a mixed extract of *Hedera helix* leaves and *Coptis chinensis*; and a composition further containing an extract(s) of *Rheum palmatum, Puerariae radix, Ginkgo* leaves, *Cassiae semen*, blueberry, bilberry, raspberry, or grape seeds, in addition to the mixed extract of *Hedera helix* leaves and *Coptis chinensis* are effective for preventing and treating diabetic complications or angioedema. According to an embodiment of the present invention, the mixed composition prepared by adding the extract(s) of *Rheum palmatum, Puerariae radix, Ginkgo* leaves, *Cassiae semen*, blueberry, bilberry, raspberry, or grape seeds, in addition to the mixed extract of *Hedera helix* leaves and *Coptis chinensis* exhibited a 2- to 10-fold inhibitory effect against the production of advanced glycation endproducts, compared with aminoguanidine, which is a positive control. Additionally, the mixed extract of *Hedera helix* leaves and *Coptis chinensis* was shown to have effects of inhibiting blood-retinal barrier breakage, formation of vascular endothelial growth factors, and formation of acellular capillaries, while also improving motor neuron conduction and nephropathy, thus confirming that the mixed extract is effective for the prevention and treatment of diabetic complications or angioedema.

The composition of the present invention may include a pharmaceutically acceptable carrier, an excipient, or a diluent, in addition to the active ingredients described above, for administration purposes.

The composition of the present invention may be formulated in the form of an oral administration such as powders, granules, tablets, capsules, suspensions, emulsions, syrups, and aerosols; external applications, suppositories, and sterile injection solutions, according to the respective conventional method to be used.

The composition of the present invention, according to the desired purpose, may be administered orally or parenterally (e.g. intravenous, subcutaneous, intraperitoneal, or topical application). The dosage may vary according to the health status, body weight, severity of a disease of a patient, drug types, administration routes, and duration, but they may be appropriately selected by one of ordinary skill in the art.

The daily dosage of the mixed extract of *Hedera helix* leaves and *Coptis chinensis* is preferably in the range of 1 mg/kg to 1,500 mg/kg, and may be administered in a few divided doses, as necessary.

Additionally, the present invention provides a method for preventing or treating diabetic complications or angioedema including administering the composition to a subject in need thereof.

The composition, diabetic complications, and angioedema are the same as explained above.

Additionally, the present invention provides a health functional food composition for preventing or ameliorating (improving) diabetic complications or angioedema containing a mixed extract of *Hedera helix* leaf and *Coptis chinensis* as an active ingredient.

Preferably, the composition of the present invention further contains an extract(s) of *Rheum palmatum, Puerariae* radix, Ginkgo leaves, Cassiae semen, blueberry, bilberry, raspberry, or grape seeds, in addition to the mixed extract of Hedera helix leaves and Coptis chinensis.

Additionally, the health functional food composition may further contain a food additive, and its acceptability as a "food additive" should be determined based on the standards and criteria regarding the corresponding items according to the General Provisions and General Test Methods of Korean Food Additives Codex approved by the Ministry of Food and Drug Safety, unless specified otherwise.

In particular, the amount of the Hedera helix leaf extract and the Coptis chinensis extract to be added to the foods including beverages during the manufacture of the health functional food may be appropriately added or reduced as necessary, and preferably, these extracts may be added in the range of 1 wt % to 15 wt % relative to 100 wt % of the food.

MODE FOR INVENTION

A better understanding of the present invention may be obtained through the following Examples and Experimental Examples. However, they are disclosed for illustrative purposes only, and should not be construed as limiting the scope of the present invention.

EXAMPLE 1

Preparation of a Composition Containing Hedera helix Leaf Extract and a Coptis chinensis Extract Dry Hedera helix leaves were added to a 30% (v/v) aqueous ethanol solution, subjected to primary and second reflux cooling extractions, and the extraction filtrate was concentrated under reduced pressure and dried to obtain a Hedera helix leaf extract.

Additionally, dry Coptis chinensis was added to a 50% (v/v) aqueous ethanol solution, subjected to primary and second reflux cooling extractions, and the extraction filtrate was concentrated under reduced pressure. The resultant was suspended in water, charged with saturated butanol, and the butanol fraction was concentrated under reduced pressure to obtain a Coptis chinensis extract.

The thus obtained Hedera helix leaf extract and the Coptis chinensis extract were mixed at a 3:1 ratio to prepare a sample, COPH.

EXAMPLE 2

Preparation of a Mixed Composition Containing a Natural Herb Extract

The COPH prepared in Example 1 was added to an extract(s) of grape seeds, Ginkgo leaves, Puerariae radix, Cassiae semen, Rheum palmatum, or bilberry at a predetermined ratio, and 15 different samples of mixed compositions containing the herbal drug extracts were prepared.

1) Preparation of a ixed Composition Containing a Hedera helix Leaf Extract, a Coptis chinensis Extract, and a Grape Seed Extract For the dry grape seed extract, Entelon® (Hanlim Pharm. Co., Ltd.) was used. The grape seed extract was mixed with COPH at a 1:1, 1:2, or 1:3 weight ratio to prepare samples of (COPH+grape seeds 1) (1:1), (COPH+grape seeds 2) (2:1), and (COPH+grape seeds 3) (3:1).

2) Preparation of a Mixed Composition Containing a Hedera helix Leaf Extract, a Coptis chinensis Extract, and a Ginkgo Leaf Extract For the Ginkgo leaf extract, Ginexin-1 (SK Chemicals Co., Ltd.) was used. The Ginkgo leaf extract was mixed with COPH at a 1:3 weight ratio to prepare a sample (COPH+Ginkgo leaves) (3:1).

3) Preparation of a Mixed Composition Containing a Hedera helix Leaf Extract, a Coptis chinensis Extract, and a Puerariae radix Extract Dry Puerariae radix was subjected to primary and secondary extraction/filtration with an 80% (v/v) aqueous ethanol solution, and concentrated under reduced pressure. The dry Puerariae radix extract was mixed with COPH at a 1:1 or 1:3 weight ratio to prepare samples of (COPH+Puerariae radix 1) (1:1) and (COPH+Puerariae radix 2) (3:1).

4) Preparation of a Mixed Composition Containing a Hedera helix Leaf Extract, a Coptis chinensis Extract, and a Cassiae semen Extract Dry Cassiae semen was subjected to primary and secondary extraction/filtration with an 80% (v/v) aqueous ethanol solution, and concentrated under reduced pressure. The dry Cassiae semen extract was mixed with COPH at a 1:1, 1:2, or 1:3 weight ratio to prepare samples of (COPH+Cassiae semen 1) (1:1), (COPH+Cassiae semen 2) (2:1), and (COPH+Cassiae semen 3) (3:1).

5) Preparation of a Mixed Composition Containing a Hedera helix Leaf Extract, a Coptis chinensis Extract, and a Rheum palmatum Extract Dry Rheum palmatum was subjected to primary and secondary extraction/filtration with a 40% (v/v) aqueous ethanol solution, and concentrated under reduced pressure. The dry Rheum palmatum extract was mixed with COPH at a 1:1, 1:2, or 1:3 weight ratio to prepare samples of (COPH+Rheum palmatum 1) (1:1), (COPH+Rheum palmatum 2) (1:2), and (COPH+Rheum palmatum 3) (1:3).

6) Preparation of a Mixed Composition Containing a Hedera helix Leaf Extract, a Coptis chinensis Extract, and a Bilberry Extract For the bilberry extract, Tagen-F® (Kukje Pharm.) was used. The bilberry extract was mixed with COPH at a 1:1, 1:2, 1:3, or 3:1 weight ratio to prepare samples of (COPH+bilberry 1) (1:1), (COPH+bilberry 2) (2:1), (COPH+bilberry 3) (3:1), and (COPH+bilberry 4) (1:3).

EXAMPLE 3

Preparation of a Composition Containing a Hedera helix Leaf Extract, a Coptis chinensis Extract, and Metformin A mixed composition containing a Hedera helix leaf extract and a Coptis chinensis extract, in the amount of 50 parts by weight, was charged with 350 parts by weight of metformin to prepare a sample COPH+MET.

EXPERIMENTAL EXAMPLE 1

Experiment on the Inhibitory Effect Against Formation of Advanced Glycation Endproducts (AGE)

Experiments were performed to examine the inhibitory effects of each of the compositions prepared in Example 1 and Example 2 against the formation of advanced glycation endproducts.

Bovine serum albumin (BSA), a protein source, was prepared by mixing into a phosphate buffer solution. As a sugar source, a mixed solution between 0.2 M fructose and 0.2 M glucose was used. Each of the compositions prepared in Example 1 and Example 2, and aminoguanidine (positive control) were respectively added into a mixed solution between BSA and a sugar, and cultured for 7 days. After culturing, the content of the resulting advanced glycation endproducts was analyzed. The amount of the advanced glycation endproducts was calculated based on the Equation 1 below using a Microplate reader (Excitation; 350 nm, Emission; 450 nm) (Table 1).

Inhibitory effect of AGE (%)={100−(fluorescence intensity of a sample)−(fluorescence intensity of a blank sample)/(fluorescence intensity of a control)−(fluorescence intensity of a blank control)}×100  [Equation 1]

TABLE 1

| Category | Conc. (μg/mL) | Inhibitory effect (%) | IC$_{50}$ (μg/mL) |
| --- | --- | --- | --- |
| COPH (*Hedera helix* leaf extract + *Coptis chinensis* extract) | 25 | 35.53 ± 4.48 | 46.05 ± 3.02 |
|  | 50 | 43.06 ± 2.82 |  |
|  | 70 | 51.08 ± 0.79 |  |
| COPH + grape seed 1 (COPH:grape seed = 1:1) | 2.5 | 15.12 ± 1.20 | 7.29 ± 0.10 |
|  | 5 | 42.02 ± 1.28 |  |
|  | 10 | 65.10 ± 0.36 |  |
| COPH + grape seed 2 (COPH + grape seed = 2:1) | 2.5 | 17.09 ± 4.48 | 18.80 ± 0.07 |
|  | 5 | 39.15 ± 1.32 |  |
|  | 10 | 60.85 ± 0.76 |  |
| COPH + grape seed 3 (COPH + grape seed = 3:1) | 2.5 | 18.03 ± 3.91 | 21.27 ± 0.58 |
|  | 5 | 39.15 ± 1.32 |  |
|  | 10 | 60.85 ± 0.76 |  |
| COPH + *Ginkgo* leaves (COPH:*Ginkgo* leaves = 3:1) | 2.5 | 25.09 ± 0.06 | 8.15 ± 0.14 |
|  | 50 | 43.98 ± 1.56 |  |
|  | 10 | 58.49 ± 1.30 |  |
| COPH + Puerariae radix1 (COPH:Puerariae radix = 1:1) | 10 | 9.41 ± 0.33 | 47.78 ± 1.24 |
|  | 25 | 23.73 ± 1.57 |  |
|  | 50 | 52.98 ± 2.06 |  |
| COPH + Puerariae radix 2 (COPH:Puerariae radix = 3:1) | 25 | 22.02 ± 2.13 | 73.53 ± 0.79 |
|  | 50 | 33.28 ± 1.86 |  |
|  | 75 | 52.13 ± 0.49 |  |
| COPH + Cassiae semen 1 (COPH:Cassiae semen = 1:1) | 10 | 19.54 ± 0.69 | 39.37 ± 0.60 |
|  | 25 | 31.18 ± 0.34 |  |
|  | 50 | 62.85 ± 0.98 |  |
| COPH + Cassiae semen 2 (COPH:Cassiae semen = 2:1) | 10 | 21.80 ± 2.20 | 46.08 ± 0.22 |
|  | 25 | 29.94 ± 1.57 |  |
|  | 50 | 54.21 ± 0.93 |  |
| COPH + Cassiae semen 3 (COPH:Cassiae semen = 3:1) | 75 | 48.39 ± 0.39 | 77.79 ± 0.24 |
|  | 100 | 56.32 ± 0.23 |  |
|  | 125 | 57.76 ± 0.15 |  |
| COPH + *Rheum palmatum* 1 (COPH:*Rheum palmatum* = 1:1) | 5 | 3.19 ± 1.25 | 21.50 ± 0.23 |
|  | 10 | 26.22 ± 0.94 |  |
|  | 25 | 57.61 ± 0.76 |  |
| COPH + *Rheum palmatum* 2 (COPH:*Rheum palmatum* = 2:1) | 10 | 7.57 ± 0.26 | 42.58 ± 1.02 |
|  | 25 | 29.50 ± 1.10 |  |
|  | 50 | 58.78 ± 1.75 |  |
| COPH + bilberry 1 (COPH:bilberry = 1:1) | 10 | 18.37 ± 0.82 | 48.13 ± 1.12 |
|  | 25 | 32.85 ± 0.66 |  |
|  | 50 | 50.92 ± 0.91 |  |
| COPH + bilberry 2 (COPH:bilberry = 2:1) | 10 | 13.62 ± 0.09 | 51.69 ± 0.21 |
|  | 25 | 20.08 ± 0.53 |  |
|  | 50 | 50.18 ± 0.09 |  |
| COPH + bilberry 3 (COPH:bilberry = 3:1) | 10 | 12.26 ± 0.37 | 42.01 ± 0.29 |
|  | 25 | 33.49 ± 0.77 |  |
|  | 50 | 58.01 ± 0.27 |  |
| COPH + bilberry 4 (COPH:bilberry = 1:3) | 5 | 23.85 ± 1.36 | 25.19 ± 0.67 |
|  | 10 | 28.66 ± 0.51 |  |
|  | 25 | 50.05 ± 0.70 |  |
| Aminoguanidine HCl (positive control) | 55.5 | 43.92 ± 0.37 | 76.47 ± 4.81 |
|  | 74.8 | 50.86 ± 2.17 |  |
|  | 92.5 | 54.91 ± 0.75 |  |

As shown in Table 1 above, it was confirmed that COPH has a 2-fold higher inhibitory effect against the formation of advanced glycation endproducts, compared to the aminoguanidine, which is a positive control.

Additionally, a mixed composition, prepared by adding an extract(s) of grape seeds, *Ginkgo* leaves, Puerariae radix, *Cassiae semen*, *Rheum palmatum*, or bilberry to COPH, also showed 2- to maximum 10-fold superior advanced glycation endproducts, compared to the aminoguanidine, which is a positive control.

EXPERIMENTAL EXAMPLE 2

Analysis of the Effect on Anti-Diabetic Complications in Zebrafish

In order to confirm the effect on of COPH anti-diabetic complications, experiments were performed to examine the inhibitory effect against the expansion of vessel diameter of vitreous body using a zebrafish embryo.

1) Preparation of a Developing Embryo of Zebrafish and Drug Treatment

A developing embryo of transgenic zebrafish (Tg(kdr: EGFP)) capable of expressing a fluorescent protein in a vascular endothelial cell was induced to have diabetes mellitus with high glucose (30 mM glucose). The resultant was administered with COPH at concentrations of 1.0 μg/mL, 5.0 μg/mL, and 10.0 μg/mL, and the effect was examined.

2) Analysis of Change in a Blood Vessel of Vitreous Body

After treating/fixing with high glucose for five days, the lens was separated and the change in the blood vessel of the vitreous body was analyzed. The COPH-treated group was shown to significantly inhibit the expansion of vessel diameter (FIG. 1). The inhibition rate against expansion of blood vessel diameter is shown in Table 2.

TABLE 2

| Treated COPH conc. (μg/mL) | 1.0 | 5.0 | 10.0 |
| --- | --- | --- | --- |
| Inhibition rate against expansion of blood vessel diameter(%) | 31.16 ± 5.96 | 44.41 ± 4.84 | 49.22 ± 5.79 |

EXPERIMENTAL EXAMPLE 3

Analysis of the Effect on Diabetic Retinal Edema and Diabetic Nephropathy in an STZ-Induced Type Diabetic Animal Model 1) Experimental Animal Six-week old male SD rats were allowed to adapt for one week, induced with STZ to have diabetes mellitus, and the resulting high glucose (above 350 mg/dL) mice were subjected to experiments. The experimental groups were divided into a normal group (NOR), a diabetes mellitus group (DM), a group treated with COPH at 25 mg/kg/day (COPH-25), and a group treated with COPH at 50 mg/kg/day (COPH-50). COPH was orally administered to each group daily for three weeks.

2) Effect of Inhibiting Blood-Retinal Barrier Breakage

For three weeks, eight rats were randomly selected from each group, retinas were separated from them, and leakage from retinal vessels was analyzed. After anesthesia, fluorescein-dextran and Hoechst 33342 were injected into the left ventricle of each mouse. In 5 minutes, eyeballs were enucleated and retinas were separated. The separated retinas were mounted on slides and observed under fluorescent microscope. For quantitative analysis, fluorescein-dextran was injected into the left ventricle, and heart blood was collected, and the remaining fluorescein-dextran was removed by perfusion, eyeballs were enucleated and then retinas were separated. The thus separated retinas were homogenized and the amount of FITC-dextran was measured only from the supernatant by spectrophotofluorometer.

Figure 2:
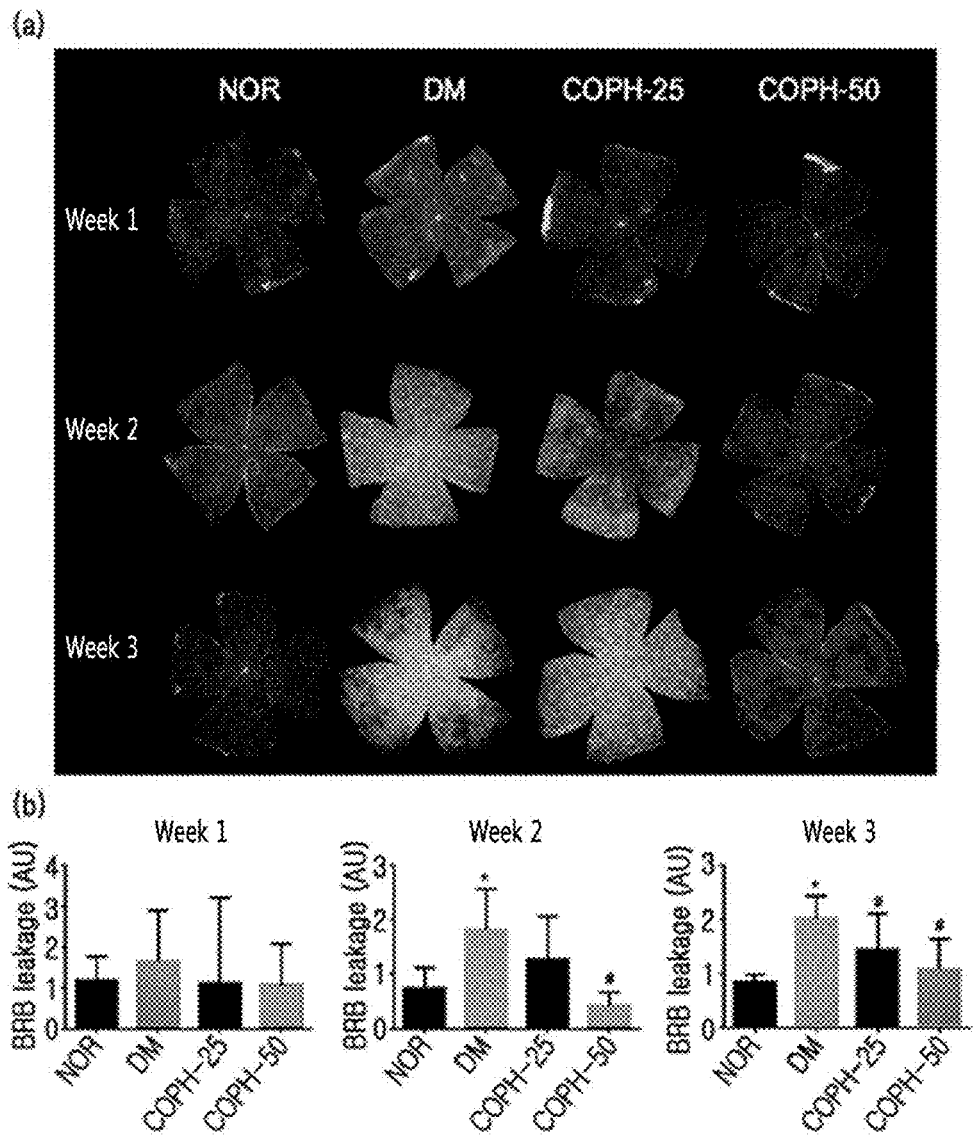
FIG. 2 shows (a) a qualitative analysis result, and (b) a quantitative analysis result of the inhibition of retinal vessel damage by COPH, in an STZ-diabetic animal model.

As shown in FIG. 2, the fluorescent material injected into the blood vessel did not leak out in the NOR group but, in the DM group, the amount of fluorescent material leaking out of the blood vessel increased with time due to blood-retinal barrier breakage, thus causing the retinal tissues to be observed brightly. In contrast, in the COPH-treated groups, the fluorescence leakage phenomenon was significantly inhibited in a dose-dependent manner (FIG. 2a). Additionally, even in the result of quantitative analysis, the amount of the fluorescent material remaining in the retina was significantly decreased in a dose-dependent manner in the COPH-treated groups (FIG. 2b). From these results, it was confirmed that COPH has excellent effects of preventing and treating diabetic retinopathy.

3) Effect of Inhibiting Diabetic Nephropathy

In order to confirm the effect of preventing (treating) nephropathy, the amounts of advanced glycation endproducts (AGEs) and 8-OHdG, which is an oxidative stress marker, in the proteinuria and urine were analyzed.

After removing impurities present in urine collected each week from each group, concentration of proteins was quantitated according to Bradford method using a Bio-Rad kit (Bio-Rad Laboratories Inc, USA).

Figure 3:
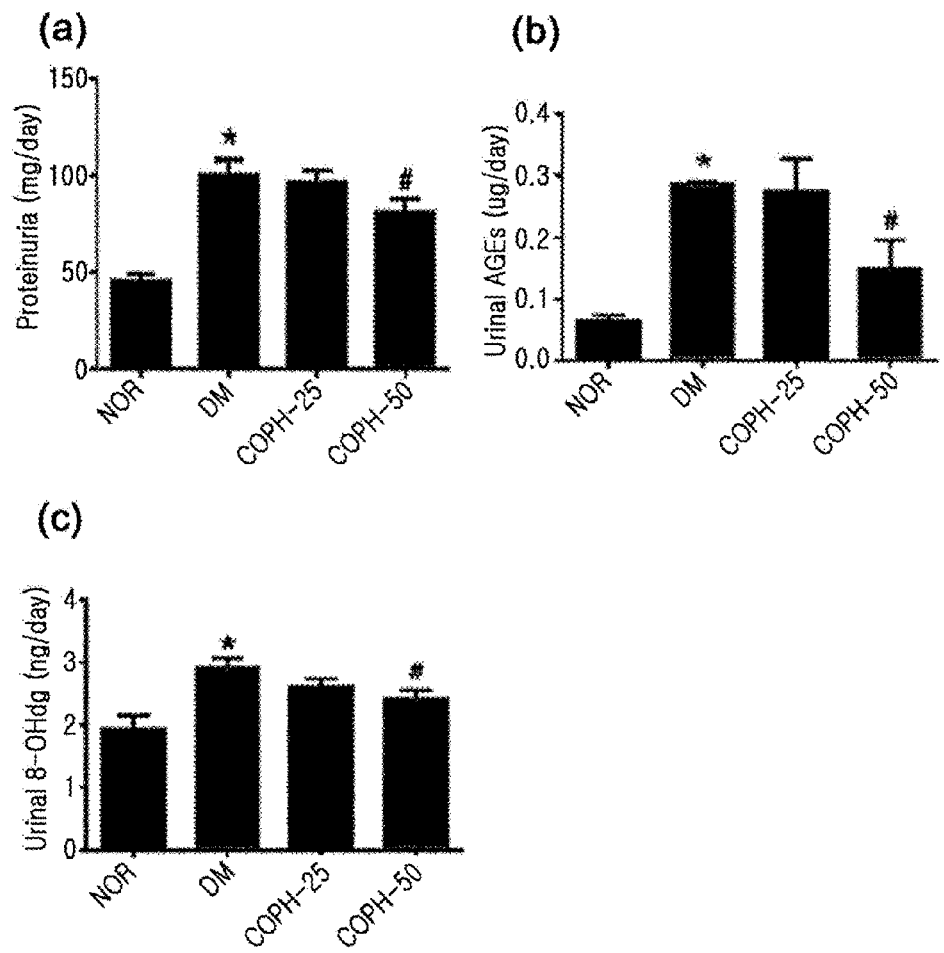
FIG. 3 shows results of the effect of COPH in lowering the amount of (a) proteinuria, (b) advanced glycation endproducts (AGEs) in urine, and (c) 8-OHdG, in an STZ-diabetic animal model.

In urine, the amounts of albumin, advanced glycation endproducts (AGEs), 8-OHdG as an oxidative stress marker, and synaptopodin were measured via ELISA (FIG. 3).

As shown in FIG. 3, the DM group showed a significantly higher increase in all three new functional markers within six weeks from the onset of diabetes mellitus compared to the NOR group. In contrast, the COPH-treated groups showed a significant decrease in a dose-dependent manner, thus implying that COPH has the preventative effect against diabetic nephropathy.

EXPERIMENTAL EXAMPLE 4

Analysis of the Effect on Diabetic Eye Disease in a Db/Db Mouse (Type 2 Diabetes Mellitus) Animal Model In order to confirm the effect of the compositions COPH and (COPH+MET) prepared in Example 1 and Example 3, respectively, on diabetic eye disease in type 2 diabetic db/db mice model, the mice were orally administered with the compositions once daily for 12 weeks. The experimental groups involved were administered as follows: the NOR group, the DM group, a metformin (350 mg/kg)-treated group (MET-350), a COPH (25 mg/kg)-treated group (COPH-25), a COPH (50 mg/kg)-treated group (COPH-50), and a mixture [COPH (50 mg/kg)+MET(350 mg/kg)]-treated group ((COPH-50)+(MET-350)).

1) Analysis of Effect of Inhibiting Blood-Retinal Barrier Breakage

After abdominal anesthesia, the mice were injected with fluorescein-dextran into the left ventricle, and the retinas were separated from the eyeballs. The thus separated retinas were mounted on slides, dried, and the degree of leakage of respective fluorescent material (FIG. 4) and serum albumin (FIG. 5) was analyzed by observation under fluorescent microscope and a staining method, thereby confirming the effect of preventing and treating the blood-retinal barrier breakage.

Figure 4:
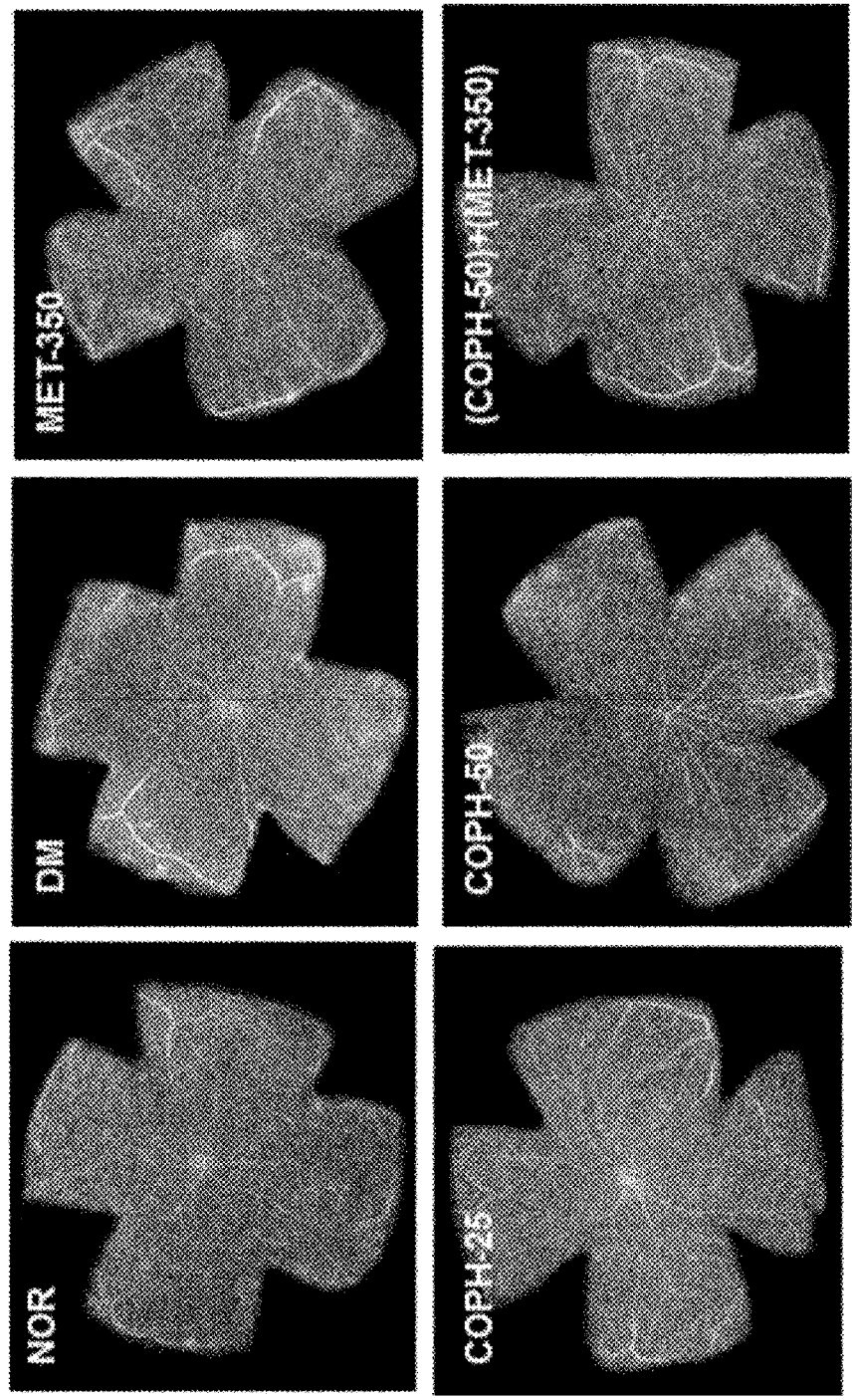
FIG. 4 shows results of the inhibitory effect of COPH or *Hedera helix* leaf extract+*Coptis chinensis* extract+metformin (COPH+MET) against retinal damage, in a diabetic animal model.

As shown in FIG. 4, the NOR group showed no leakage phenomenon, whereas, in the DM group, the fluorescent material leaked out of the blood vessel in most mice due to the blood-retinal barrier breakage and accumulated thus making them brighter than the NOR group. Meanwhile, the metformin-treated group (MET) showed a leakage of the fluorescent material and the brightness was reduced compared to that of the DM group. In the COPH-treated groups, the brightness due to the leakage of the fluorescent material was decreased in a dose-dependent manner, and in particular, the high dose COPH-treated group showed a significant decrease in the leakage of the fluorescent material. Additionally, the (COPH+MET) mixture-treated group showed the most excellent inhibitory effect, thus implying that the most excellent inhibitory effect is due to the synergistic effect of COPH and metformin.

Figure 5:
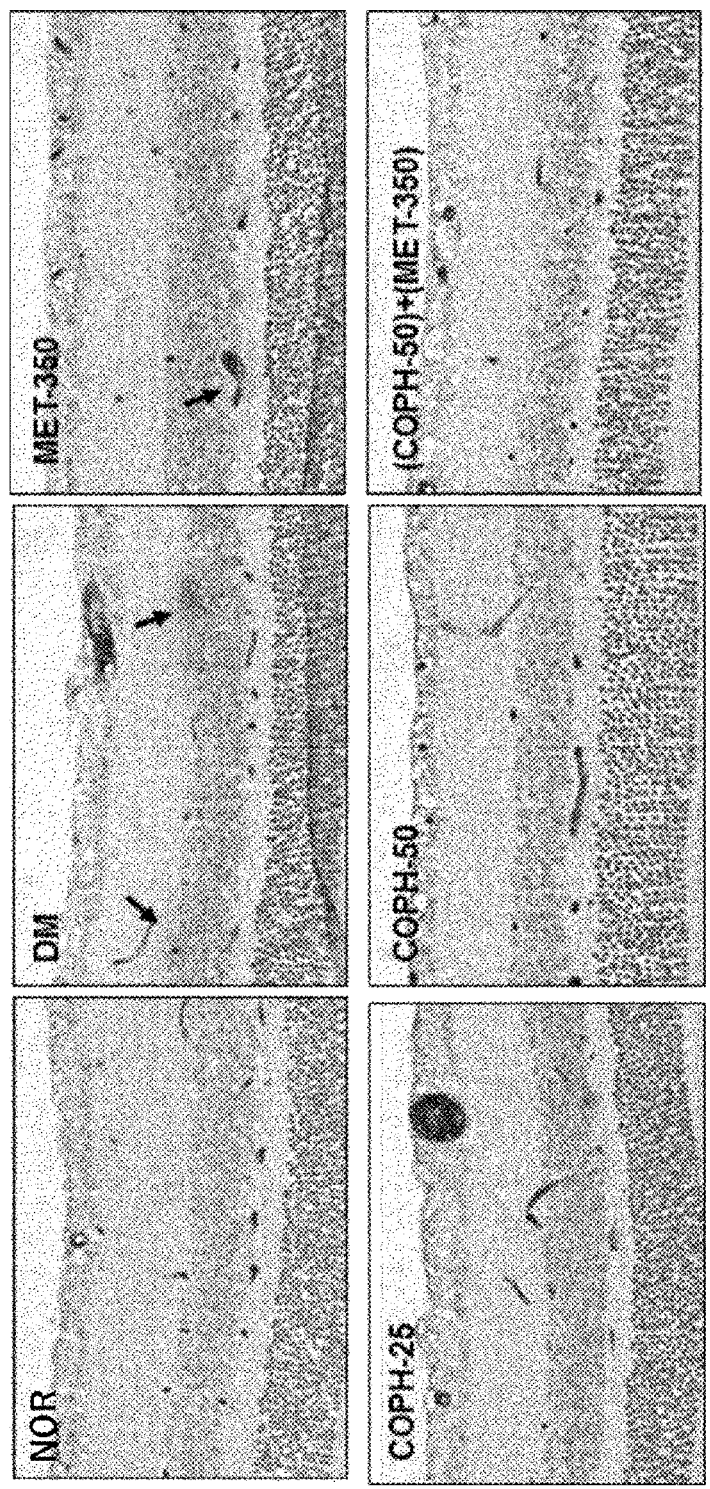
FIG. 5 shows results of the inhibitory effect of COPH or (COPH+MET) against the release of serum albumin from retinal vessels, in a diabetic animal model.

Additionally, as shown in FIG. 5, in the DM group, albumin leaked out of the blood vessel and stained (arrow) the neighboring area with a hazy brown color. However, the high-dose COPH-treated group and the (COPH+MET) mixture-treated group did not show the above phenomenon.

2) Immunohistochemical Staining Analysis

The effects of inhibiting damage in interstitial tight junction proteins, inhibiting the expression of matrix metalloproteinase-2, inhibiting accumulation of advanced glycation endproducts, and inhibiting formation of vascular endothelial growth factor were confirmed via immunohistochemical stain analysis (FIGS. 6 to 9).

Figure 6:
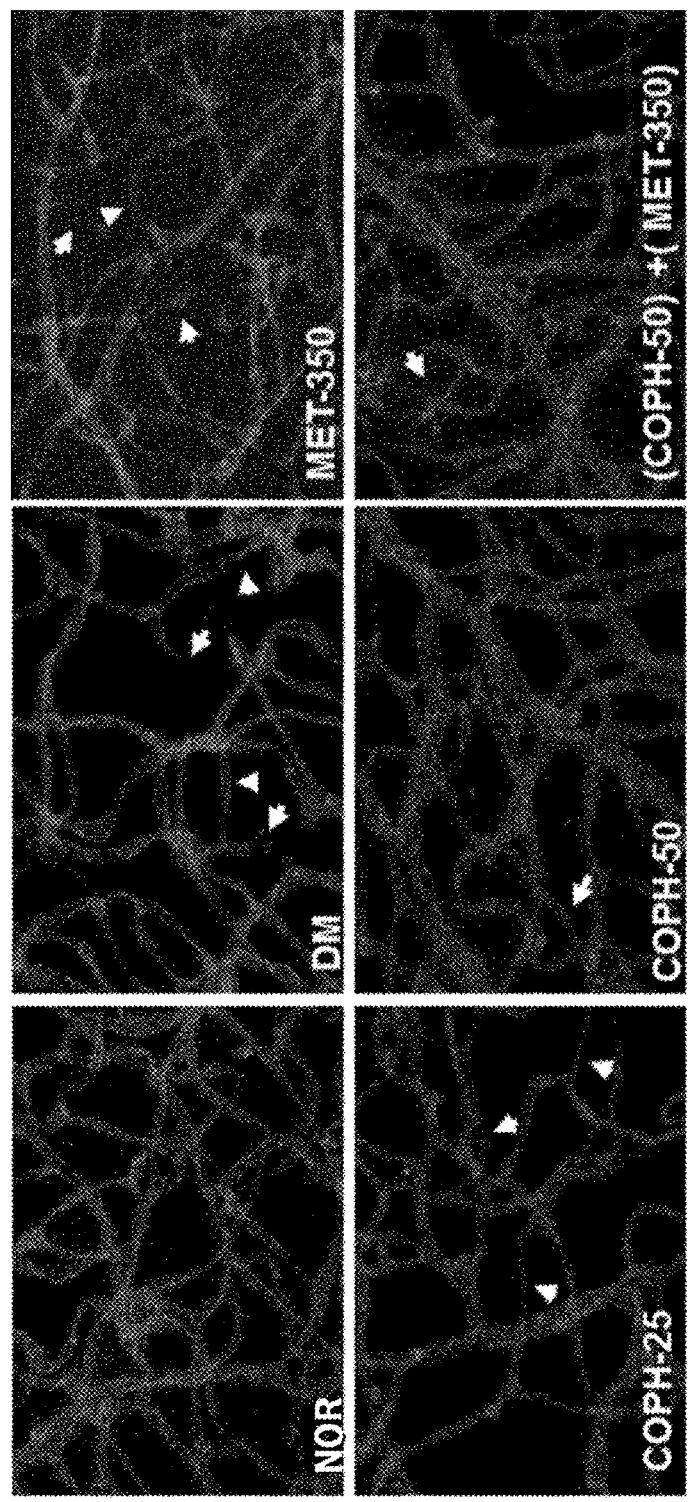
FIG. 6 shows results of the inhibitory effect of COPH or (COPH+MET) against the loss of occluding, in the retina of a diabetic animal model.

(1) Analysis of Effect of Inhibiting Damage on Interstitial Tight Junction Proteins As shown in FIG. 6, the DM group showed that the skein-like connecting lines of occlusion became cut off in various blood vessels (arrow). However, the COPH-treated groups and the (COPH+MET) mixture-treated group were shown to prevent (treated) the loss of occlusion.

(2) Analysis of Effect of Inhibiting the Expression of Matrix Metalloproteinase-2 (MMP2)

Figure 7:
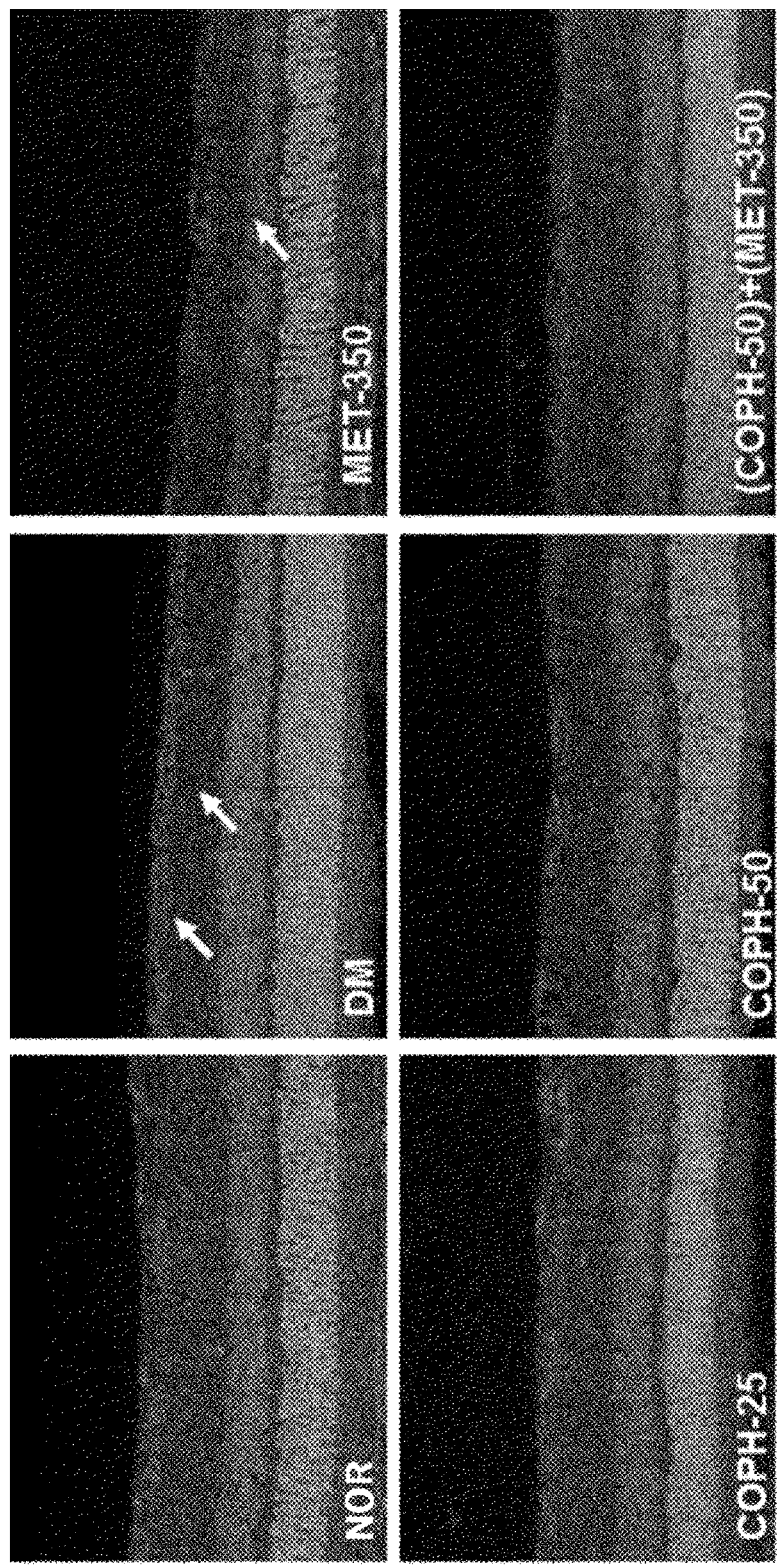
FIG. 7 shows results of the inhibitory effect of COPH or (COPH+MET) against the expression of Matrix metalloproteinase-2 (MMP2), in the retina of a diabetic animal model.

As shown in FIG. 7, the DM group showed an increase in the expression of MMP2 (arrow), whereas the expression of MMP2 was inhibited in the COPH-treated groups and the (COPH+MET) mixture-treated group.

Figure 8:
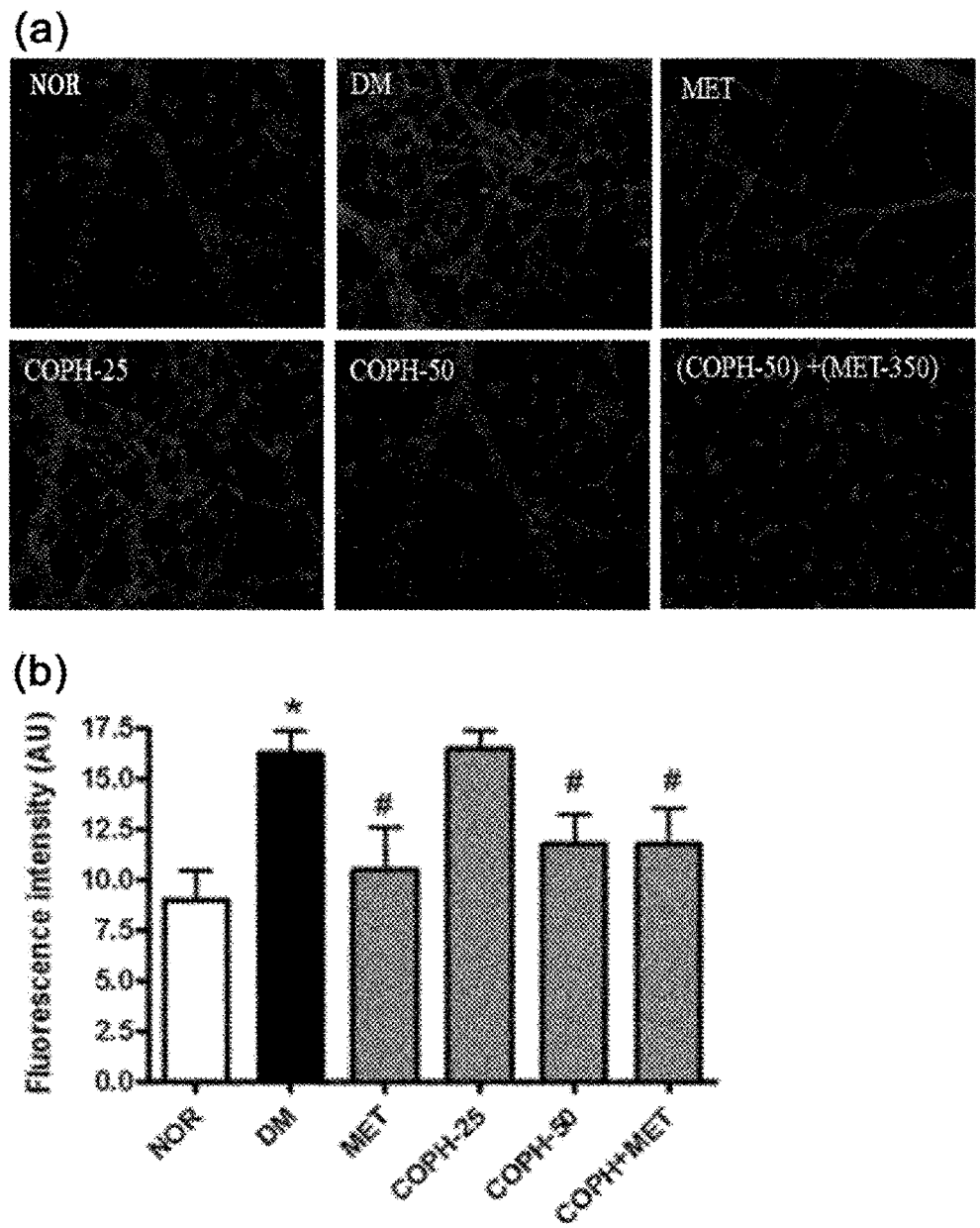
FIG. 8 shows (a) a qualitative analysis result, and (b) a quantitative analysis result of the inhibition of formation of advanced glycation endproducts (AGEs) by COPH or (COPH+MET), in the retinal vessel of a diabetic animal model.

(3) Analysis of Effect of Inhibiting the Formation of Advanced Glycation Endproducts within Retinal Vessels As shown in FIG. 8, the DM group showed about a 2-fold higher formation of advanced glycation endproducts, compared to the NOR group, whereas the COPH-treated groups and the (COPH+MET) mixture-treated group significantly inhibited the formation of the advanced glycation endproducts.

(4) Analysis of Effect of Inhibiting the Formation of Vascular Endothelial Growth Factor (VEGF)

VEGF induces neovascularization and increases permeability of blood vessels. Additionally, VEGF also induces the formation of substrate-degradative proteins. Accordingly, it was confirmed whether the effect of the COPH-treated groups and the (COPH+MET) mixture-treated group inhibiting the vascular permeability was due to the inhibition of formation of vascular endothelial growth factor (FIG. 9).

Figure 9:
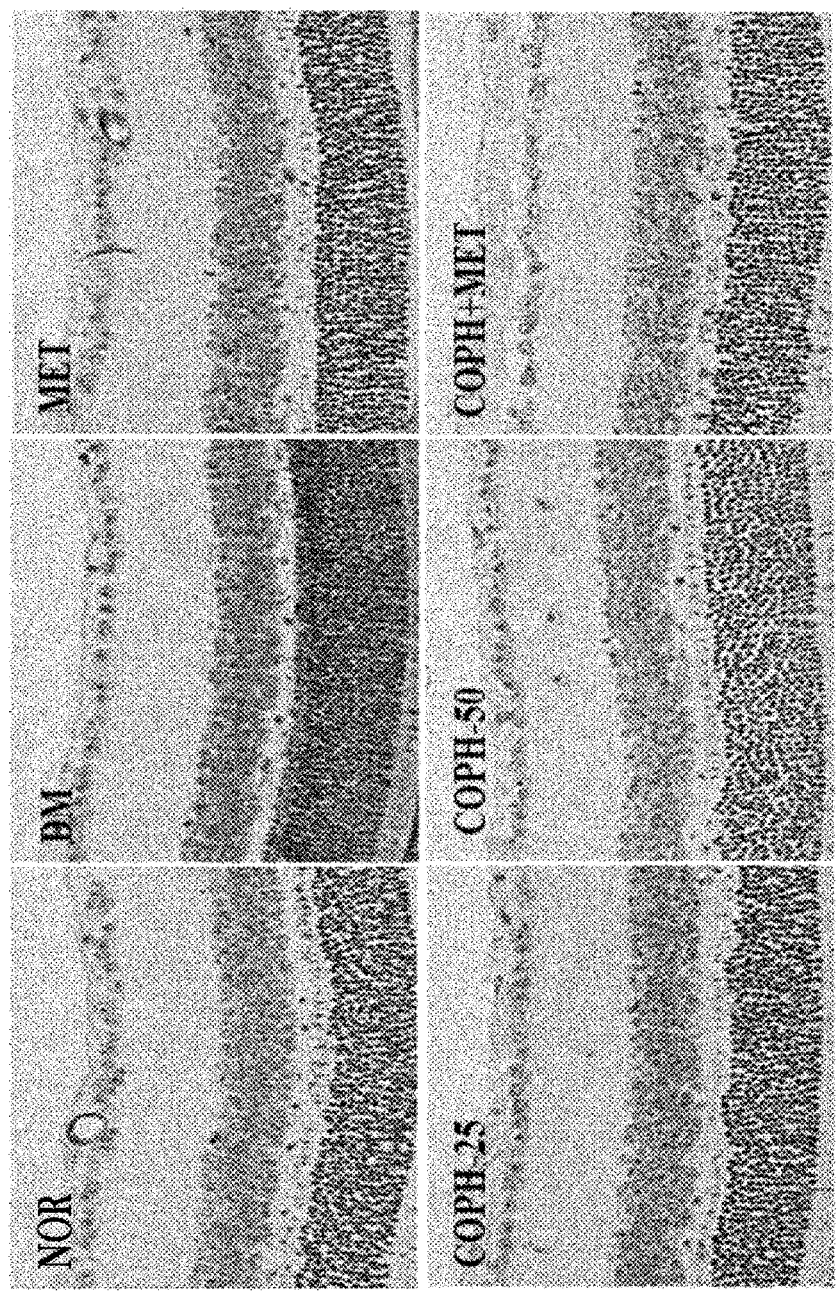
FIG. 9 shows a qualitative analysis result of the inhibition of formation of retinal vascular endothelial growth factor (VEGF) by COPH or (COPH+MET), in a diabetic animal model.

As shown in FIG. 9, the DM group apparently increased the formation of VEGF within the retinal tissue, and the COPH-treated groups, the MET group, and the (COPH+MET) mixture-treated group significantly inhibited the expression of VEGF.

3) Analysis of Effect of Inhibiting Acellular Capillary Formation

One of the early symptoms of diabetic retinopathy is that, due to acellular capillary formation, the nuclei of the adjacent pericytes are apoptosized, thus progressing into retinopathy. After enucleation of retinas from the eyeballs, they were washed and cultured. The internal membrane was removed from the digested retina. The vascular membrane was separated from the retina background, dried and then the change in cell wall and nuclei were observed (FIG. 10).

Figure 10:
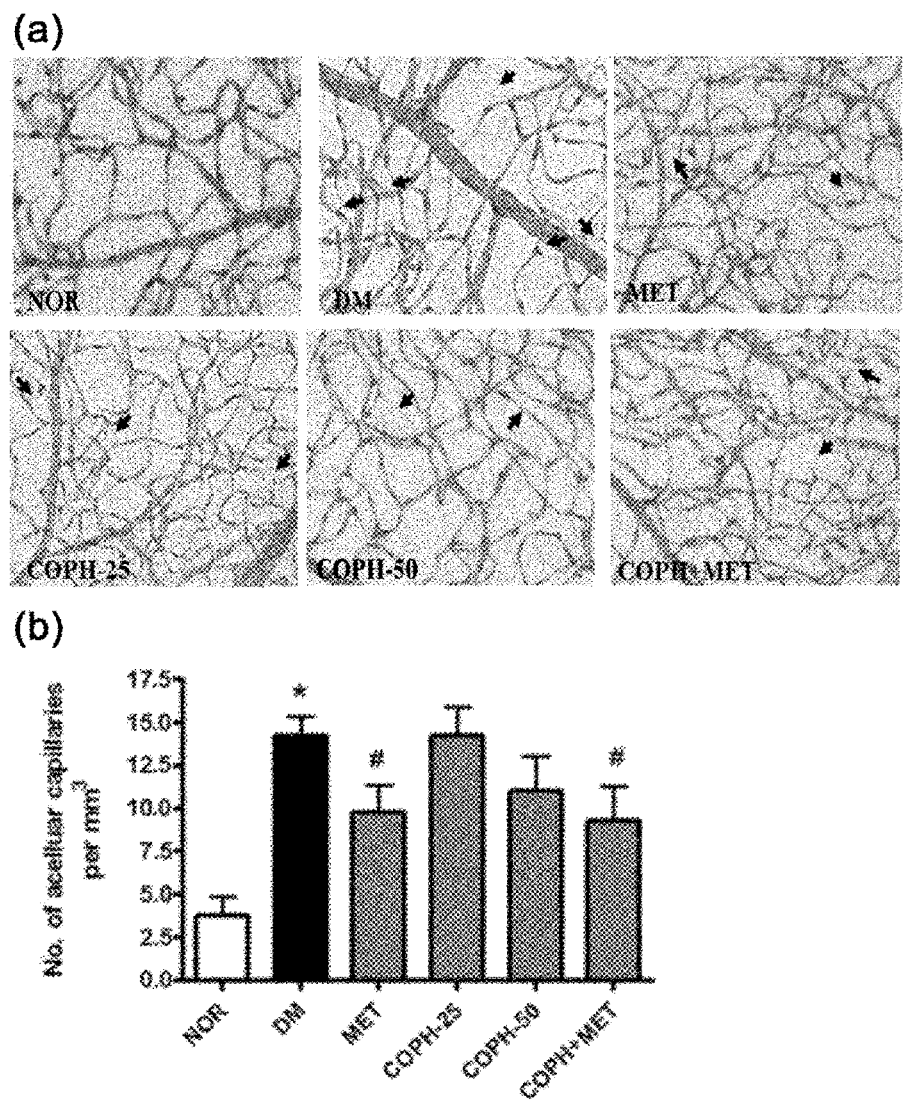
FIG. 10 shows (a) a qualitative analysis result, and (b) a quantitative analysis result of the inhibition of retinal acellular capillary formation by COPH or (COPH+MET), in a diabetic animal model.

As shown in FIG. 10, as a result of analysis of the number of acellular capillaries of each group, the DM group showed about a 5-fold increase in the number of acellular capillaries, whereas the acellular capillary formation was significantly inhibited in the COPH-treated groups and the (COPH+MET) mixture-treated group.

4) TUNEL Staining Analysis

One of the major causes that contribute to blindness from diabetic retinopathy is the loss of the optic nerve. Loss of the optic nerve generally occurs due to apoptosis triggered by high glucose level in the body. Accordingly, the presence of apoptosis of the retinal optic nerve was confirmed via TUNEL staining analysis, which enables determination of cell apoptosis using a retina specimen (FIG. 11).

Figure 11:
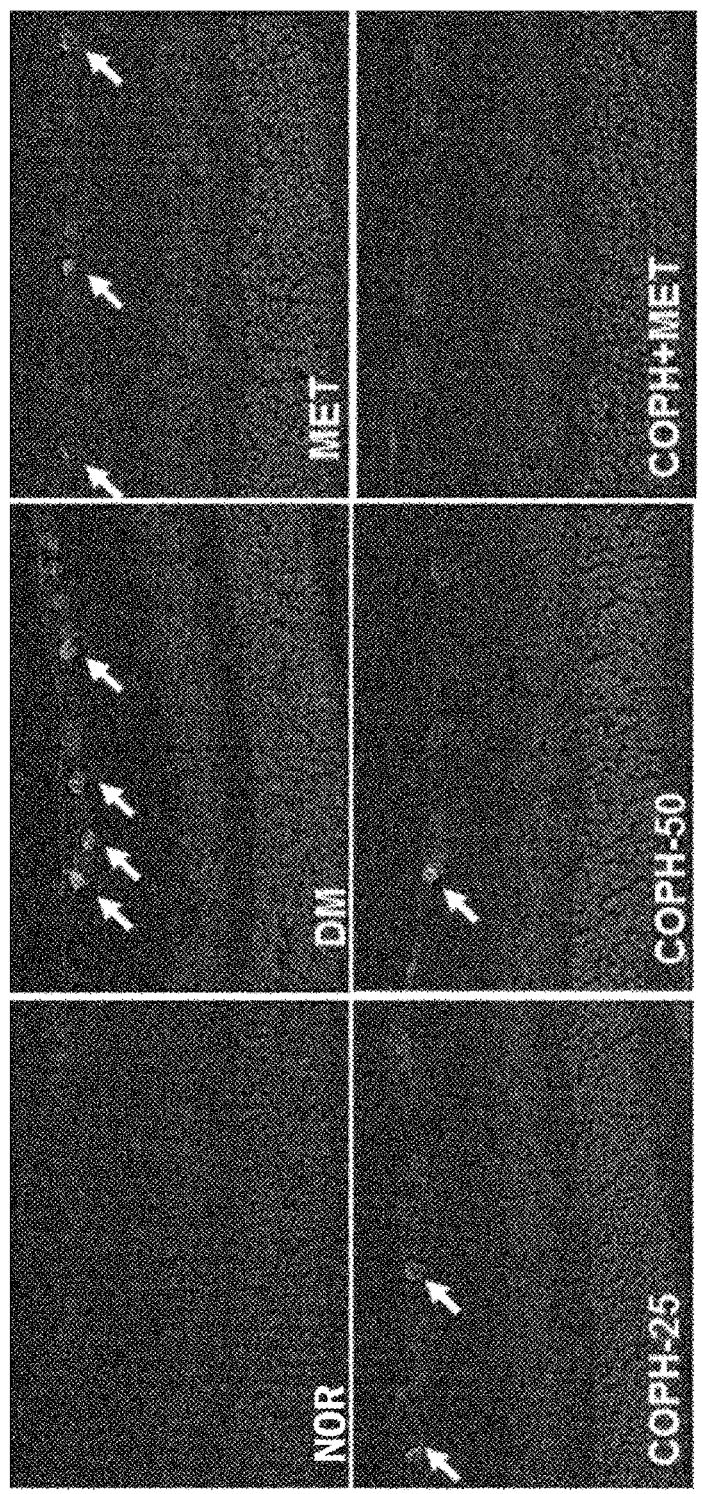
FIG. 11 shows results of the inhibitory effect of COPH or (COPH+MET) against the retinal neuronal damage, in a diabetic animal model.

As shown in FIG. 11, in the DM group, the nuclei of the retinal ganglion cells exhibit strong fluorescent responses (arrow), but the neuronal apoptosis was inhibited in the COPH-treated groups and the (COPH+MET) mixture-treated group in a dose-dependent manner.

5) Analysis of Effect of Inhibiting Oxidative Stress

Reactive oxygen species (ROS) or reactive nitrogen species (RNS) induced by high glucose can damage retinal cells. Their inhibitory effects were analyzed by staining with 8-OHdG (an indicator of ROS) and nitrotyrosine (an indicator of RNS) (FIG. 12).

Figure 12:
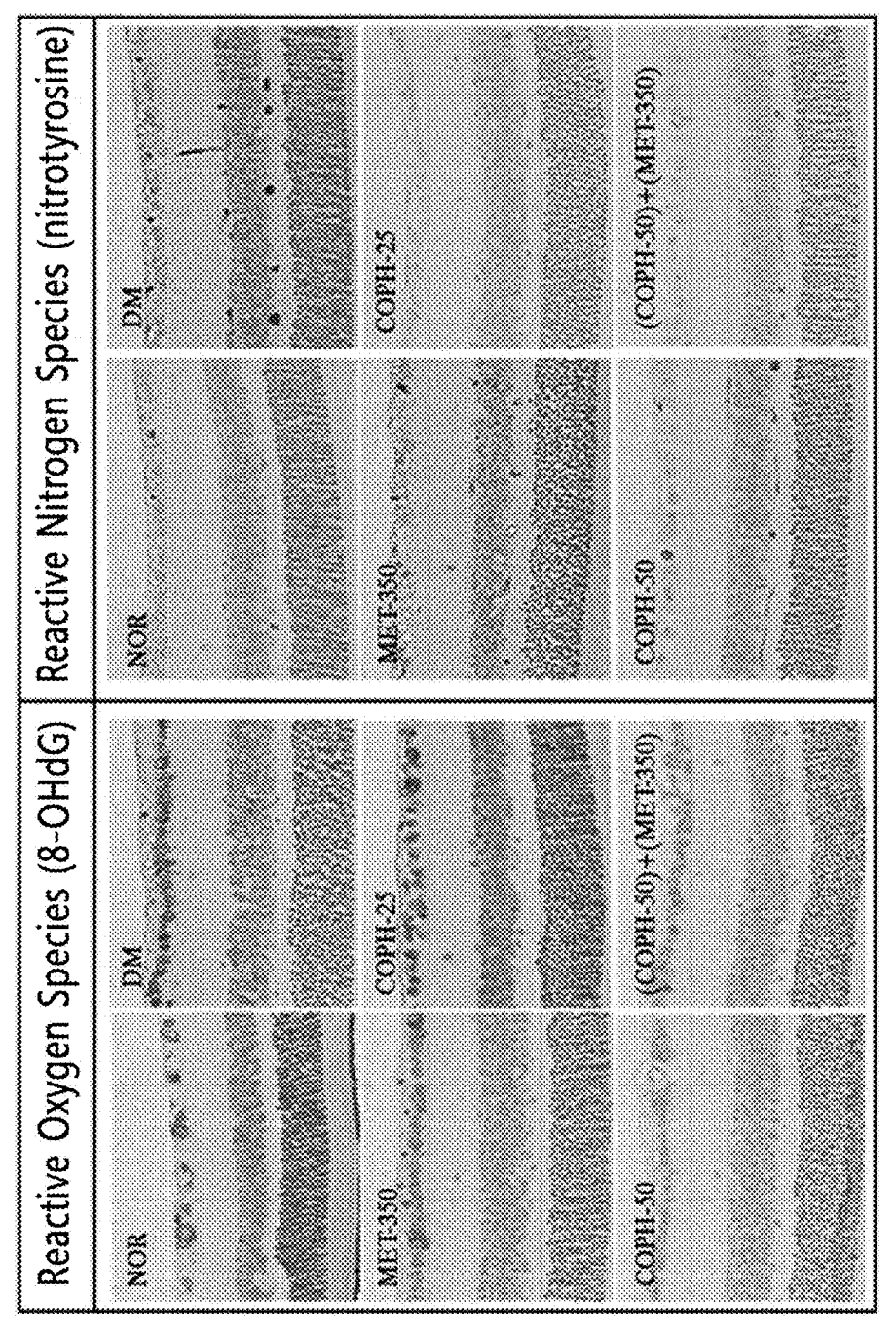

As shown in FIG. 12, the DM group strongly expressed the two indicators, whereas the COPH-treated group showed a decrease of the expression in a dose-dependent manner, and the high-dose COPH-treated group and the (COPH+MET) mixture-treated group exhibited excellent inhibitory effects against the expression of the two indicators.

EXPERIMENTAL EXAMPLE 5

Analysis of the Effect on Diabetic Neuropathy in a Db/Db Mouse (Type 2 Diabetes Mellitus) Animal Model In order to confirm the effect of COPH for preventing (treating) neuropathy in a diabetic animal model, the delay phenomenon in motor neuron conduction was measured.

1) Experimental Animals

Male db/db mice with a blood glucose level of 350 mg/dL or higher were selected and orally administered once daily for six weeks. The experimental groups involved were the NOR group, the DM group, the COPH (25 mg/kg)-treated group (COPH-25), and the COPH (50 mg/kg)-treated group (COPH-50).

2) Motor Neuron Conduction Velocity (MNCV)

Figure 13:
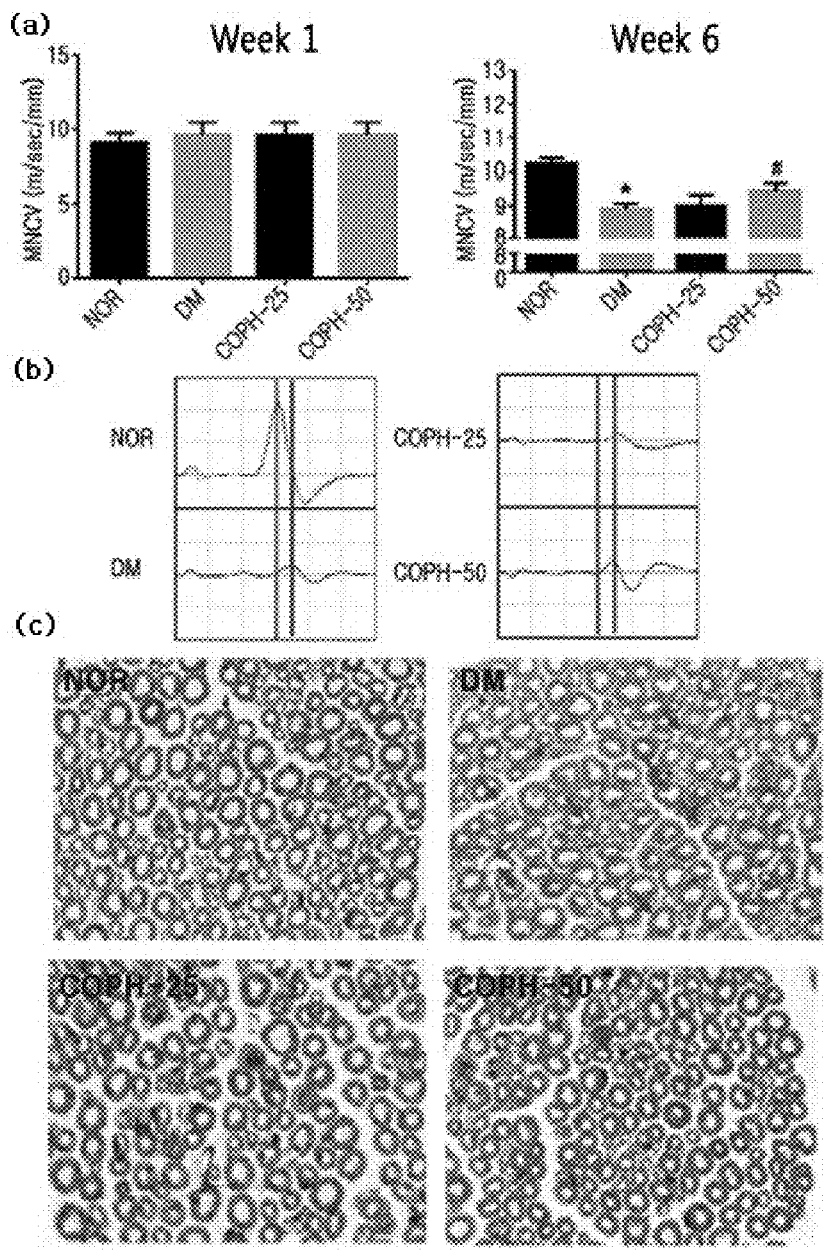
FIG. 13 shows results of improvement in motor neuron conduction velocity (MNCV) by COPH (FIGS. 13a and 13b), and the presence of denatured myelin (FIG. 13c), in a diabetic animal model.

After anesthetizing the mice, they were fixed on a warm plate, and motor neuron conduction velocity was measured on caudal neurons using a neuron conduction velocity measuring device (AD Instrument, Australia). An electric stimulus was applied to a caudal origin of each mouse, and the active potential was recorded. The active electrode was placed at a 1 cm interval from the control electrode. The measurements were made based on stimulus time of 0.1 msec, filtration frequency of 10 Hz to 10 kHz, recording sensitivity of 5 mV/div, and a recording speed of 1 ms/div. A total of 10 measurements were made and an average value was obtained therefrom (FIG. 13).

As shown in FIGS. 13a and 13b, the DM group, six weeks after the induction of diabetes mellitus, showed a decrease in motor neuron conduction velocity compared to the NOR group. However, the COPH-treated group showed an improvement of the motor neuron conduction velocity in a dose-dependent manner, and the COPH-50 group showed a significant improvement in the motor neuron conduction velocity.

3) Demyelination of Nerve Fiber Bundle

The presence of demyelination, which is a cause of the delay in motor neuron conduction velocity of nerve fibers, in diabetic neuropathy was examined. The cross-sections of the nerve fiber bundles of sciatic nerves were specially stained. As a result, a circular shape of myelin was observed in the NOR group showed, whereas numerous deformed myelins (arrow) were observed in the DM group. However, the number of the deformed myelins decreased in a dose-dependent manner in the COPH-treated groups (FIG. 13c).

EXPERIMENTAL EXAMPLE 6

Experiments on Effect of COPH on Anti-Diabetic Complications in STZ-Induced Type 1 Diabetes Mellitus Animal Model Mice According to Weeks In order to confirm the effect of COPH in preventing and treating diabetic retinopathy, the effect after COPH administration was analyzed five times at week 1, week 2, week 3, week 6, and week 12.

1) Experimental Animals

Male SD rats were induced to have an STZ (60 mg/kg), and those having a blood glucose level of 350 mg/dL or higher were selected and subjected to experiments. The experimental groups involved were (1) the NOR group, (2) the DM group, (3) the COPH (25 mg/kg)-treated group (COPH-25), and (4) the COPH (50 mg/kg)-treated group (COPH-50). The drugs were orally administered once daily, and the effect according to weeks was examined five times in week 1, week 2, week 3, week 6, and week 12 after the administration.

2) Histopathological Examination

In order to observe the pathological changes in tissues, H&E staining and PAS staining were performed.

3) Western Blotting Analysis

After the quantitative estimation of proteins according to Lowry, the proteins were subjected to SDS-PAGE gel electrophoresis. The amount of proteins was measured based on density via the Scion Image Analysis Program.

4) Blood-Retinal Barrier Breakage

Figure 14A:
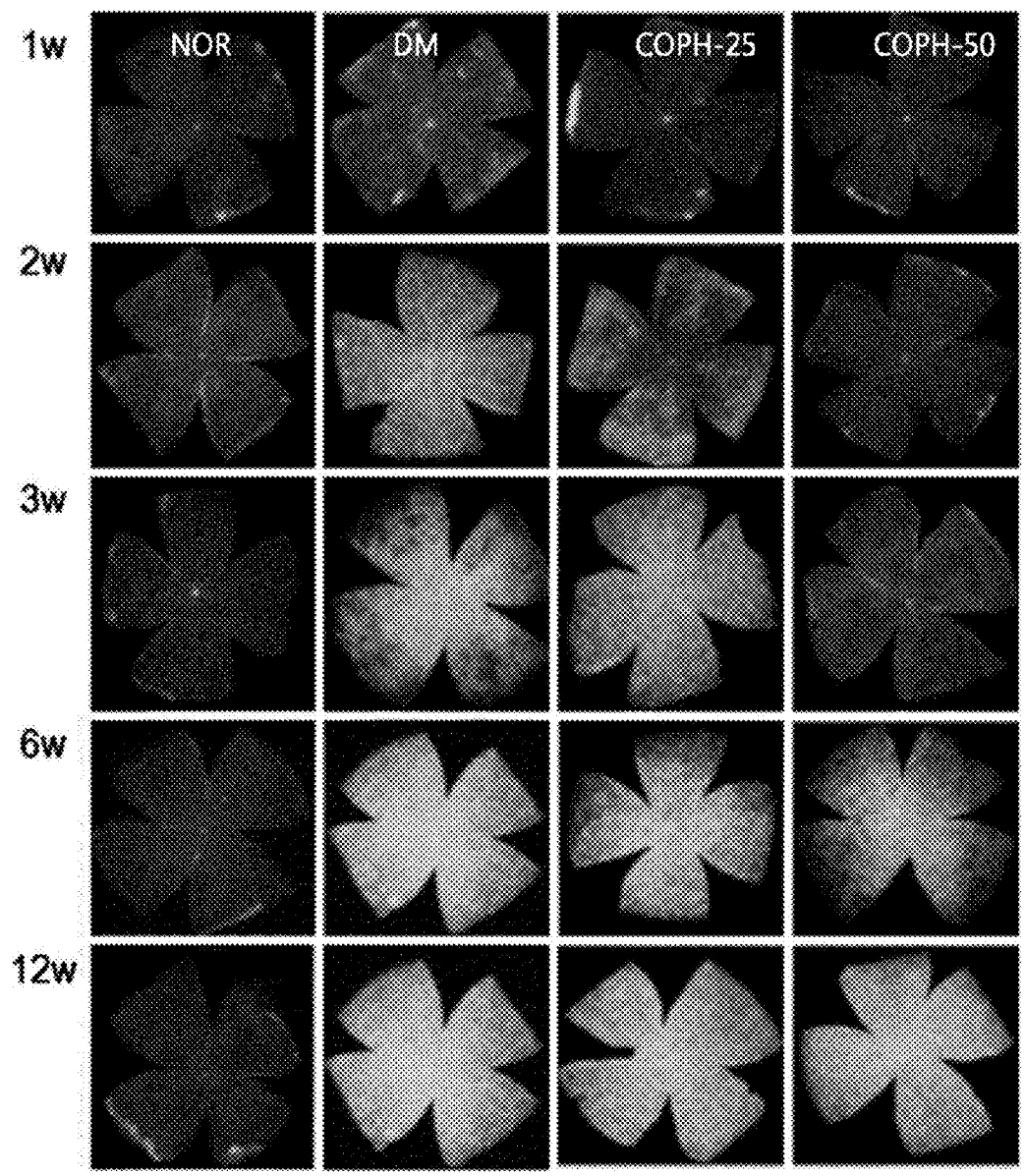
FIG. 14 shows (a) a qualitative analysis result, and (b) a quantitative analysis result of the inhibition of retinal vessel damage by COPH, in a diabetic animal model.
Figure 14B:
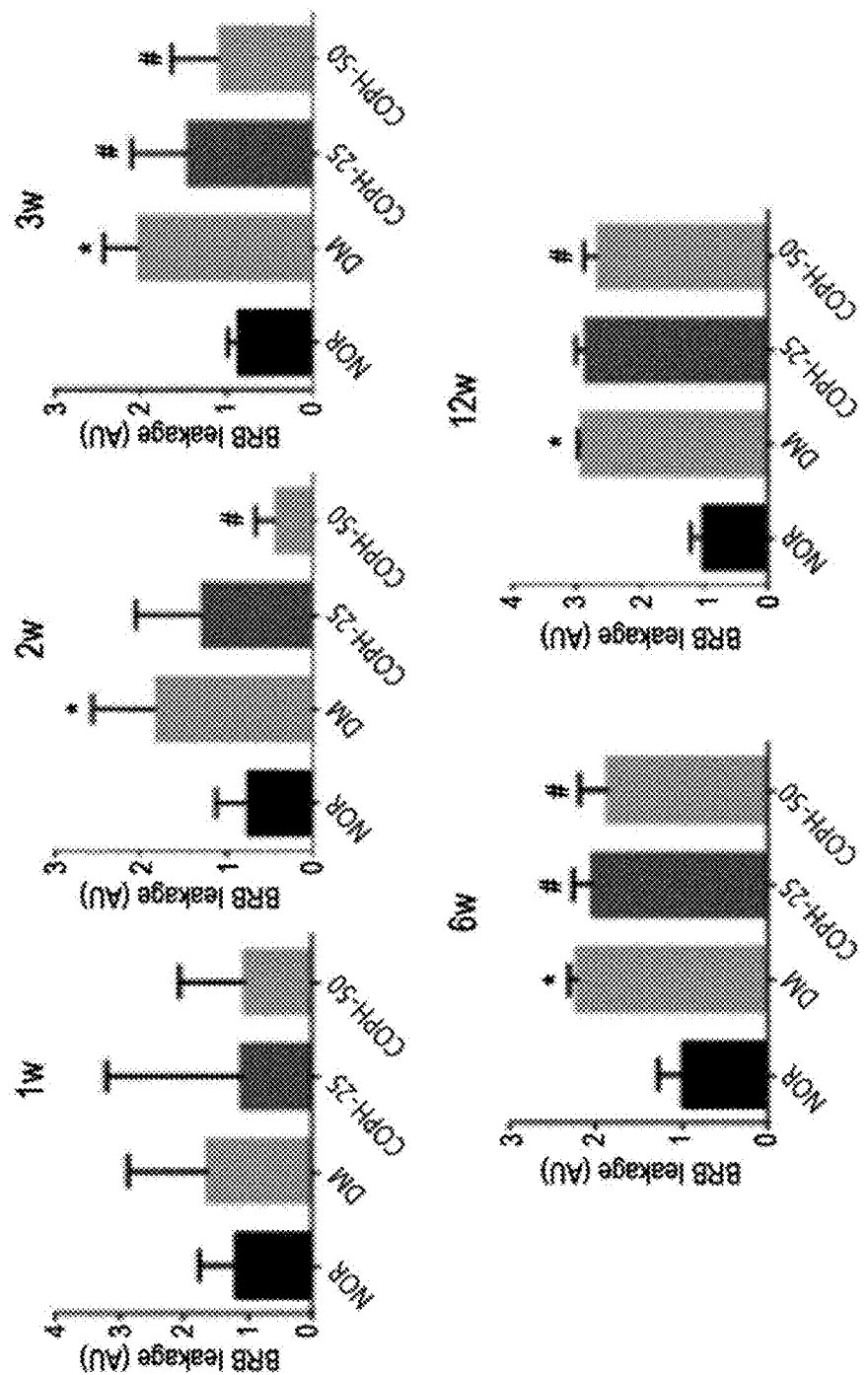

As shown in FIG. 14, the phenomenon of fluorescent material leakage due to the blood-retinal barrier breakage was analyzed in week 1, week 2, week 3, week 6, and week 12 after the drug administration. The DM group showed a significant increase in the distinct leakage of fluorescent materials from two weeks after the onset of the experiment. However, the COPH-treated groups (COPH-25 group and COPH-50 group) significantly inhibited the leakage of fluorescent materials from three weeks after the onset of the experiment.

EXPERIMENTAL EXAMPLE 7

Analysis of the Inhibitory Effect Against Blood-Retinal Barrier Breakage in a VEGF-Induced Animal Model 1) Experimental Animals Seven-week old male SD rats were respectively injected with a rat VEGF protein (Vascular endothelial growth factor, R&D research, USA) into their left eyeballs to induce a blood-retinal barrier breakage. Since the amount of vitreous body present inside a murine eyeball is approximately 50 µL to 55 µL, drugs are at concentrations of 12 µg/mL, 60 µg/mL, and 120 µg/mL, which are at least 12 times more concentrated than the final concentration in murine eyeballs.

2) Analysis of Blood-Retinal Barrier Breakage

Twenty-four hours after the drug administration, each mouse was anesthetized to secure its heart, and fluorescein-dextran was injected into its left ventricle. After enucleation of an eyeball from each mouse, the retina was separated from the eyecup, in the case of the left eyeball. The separated retinas were mounted on slides, dried, and observed. For quantitative analysis, a blood sample was collected after injecting fluorescein-dextran into the left ventricle of each mouse, and the fluorescein-dextran remaining in the blood vessel was removed and then the retina was separated. The separated retina was centrifuged and the fluorescence of the supernatant was measured via ELISA reader (FIG. 15).

Figure 15A:
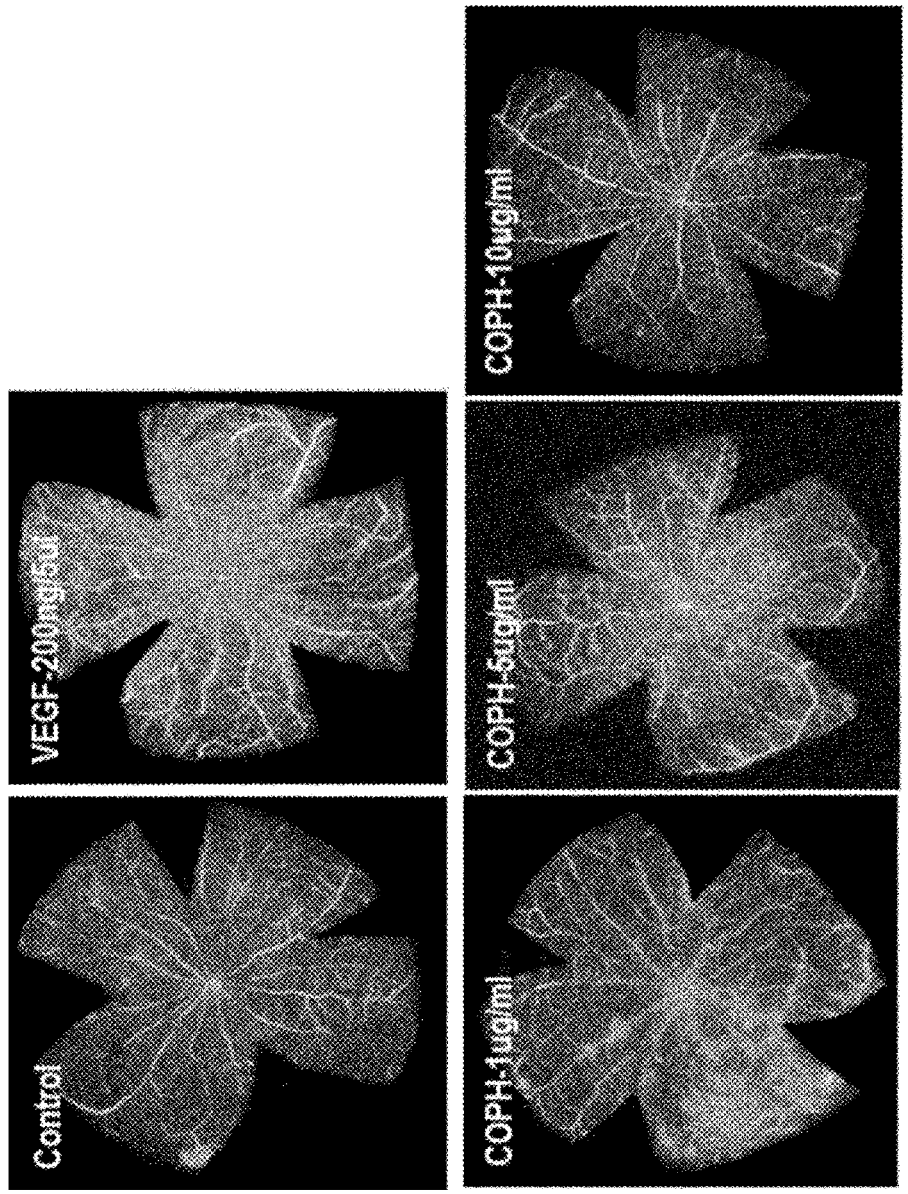
FIG. 15 shows (a) a qualitative analysis result, and (b) a quantitative analysis result of the inhibition of blood-retinal barrier breakage by COPH, in a VEGF-induced animal model.

As shown in FIG. 15a, the NOR group showed no noticeable leakage of any fluorescence, but the leakage of fluorescent materials out of the blood vessels was observed in all of the individual mice in the group treated with VEGF into the eyeballs. In contrast, the COPH-treated groups showed a decreased leakage of fluorescent materials due to VEGF, thus confirming that the intensity of fluorescence decreased in a dose-dependent manner.

Figure 15B:
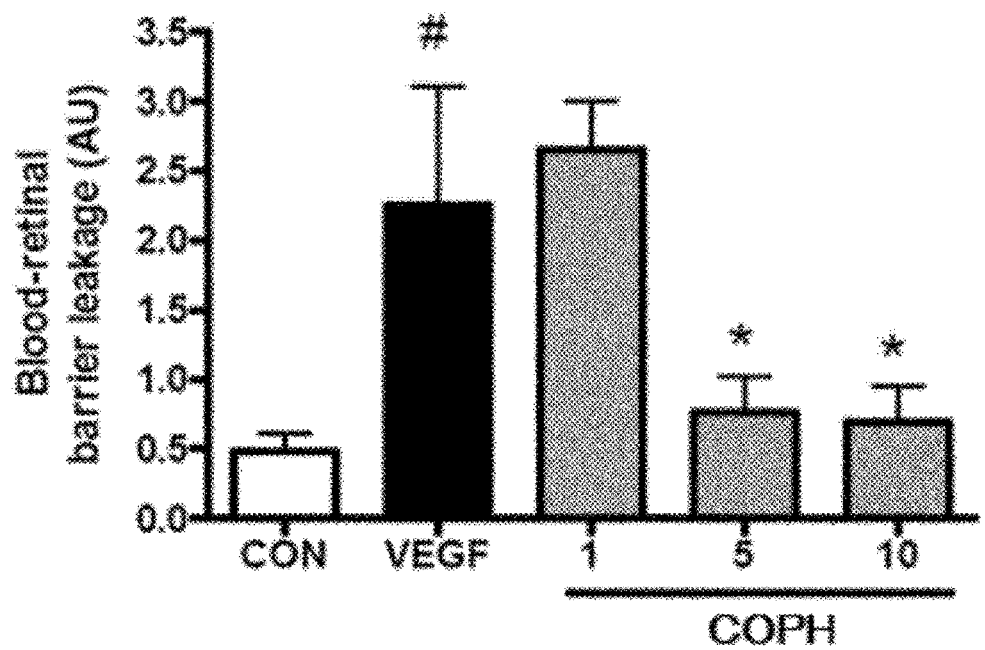

Additionally, as shown in FIG. 15b, the result of quantitative analysis also showed a 5-fold increase in the leakage of fluorescence materials out of the blood vessels in the VEGF-treated group (VEGF) compared to that of the CON group, whereas the COPH-treated groups showed a dose-dependent decrease, and in particular, the COPH (5 mg/kg)-treated group and the COPH (10 mg/kg)-treated group showed a significant inhibition of fluorescence leakage caused by the blood-retinal barrier breakage, comparable to the level of the CON group.

The invention claimed is:

1. A method of preventing or treating diabetic complications or angioedema, comprising administering a pharmaceutical composition to a subject in need thereof, wherein the composition comprises a mixed ethanol extract of *Hedera helix* leaves and *Coptis chinensis* as an active ingredient.

2. The method according to claim 1, wherein the composition is prepared by mixing a *Hedera helix* leaf ethanol extract and a *Coptis chinensis* ethanol extract at a ratio of 10:1 to 1:10, or by mixing *Hedera helix* leaves and a *Coptis chinensis* at a ratio of 10:1 to 1:10, followed by ethanol extraction.

3. The method according to claim 1, wherein the composition further comprises an extract of *Rheum palmatum, Puerariae radix, Ginkgo* leaves, *Cassiae semen*, blueberry, billberry, raspberry, or grape seeds.

4. The method according to claim 1, wherein the composition further comprises metformin.

5. The method according to claim 1, wherein the ethanol extraction is subject to reflux cooling extraction.

6. The method according to claim 1, wherein the diabetic complication is diabetic ocular disease, diabetic retinopathy, diabetic cataract, diabetic nephropathy, diabetic neuropathy, diabetic cancer, diabetic heart disease, diabetic osteoporosis, or diabetic arteriosclerosis.

7. The method according to claim 1, wherein the angioedema is varicose veins, macular edema, or macular degradation.

8. A method for preventing or ameliorating diabetic complications or angioedema, comprising administering a functional food composition to a subject in need thereof, wherein the food composition comprises a mixed ethanol extract of *Hedera helix* leaves and *Coptis chinensis* as an active ingredient.

9. The method according to claim 8, wherein the composition is prepared by mixing a *Hedera helix* leaf ethanol extract and a *Coptis chinensis* ethanol extract at a ratio of 10:1 to 1:10, or by mixing *Hedera helix* leaves and a *Coptis chinensis* at a ratio of 10:1 to 1:10, followed by ethanol extraction.

10. The method according to claim 8, wherein the composition further comprises an extract of *Rheum palmatum, Puerariae radix, Ginkgo* leaves, *Cassiae semen*, blueberry, billberry, raspberry, or grape seeds.

11. The method according to claim 8, wherein the extraction is subject to reflux cooling extraction.

12. The method according to claim 8, wherein the diabetic complication is diabetic ocular disease, diabetic retinopathy, diabetic cataract, diabetic nephropathy, diabetic neuropathy, diabetic cancer, diabetic heart disease, diabetic osteoporosis, or diabetic arteriosclerosis.

13. The method according to claim 8, wherein the angioedema is varicose veins, macular edema, or macular degradation.

* * * * *